US011980485B1

(12) United States Patent
Li et al.

(10) Patent No.: US 11,980,485 B1
(45) Date of Patent: May 14, 2024

(54) METHOD AND SYSTEM FOR DETERMINING A TREATMENT OUTCOME PREDICTION FOR A PATIENT BASED ON ELECTROENCEPHALOGRAPH

(71) Applicant: Neumarker, Inc, Palo Alto, CA (US)

(72) Inventors: Qiang Li, Saratoga, CA (US); Qing Wang, Palo Alto, CA (US)

(73) Assignee: Neumarker, Inc, Palo Alto, CA (US)

( * ) Notice: Subject to any disclaimer, the term of this patent is extended or adjusted under 35 U.S.C. 154(b) by 0 days.

(21) Appl. No.: 18/090,037

(22) Filed: Dec. 28, 2022

(51) Int. Cl.
*A61B 5/00* (2006.01)
*A61B 5/369* (2021.01)
*G16H 15/00* (2018.01)

(52) U.S. Cl.
CPC ............ *A61B 5/7275* (2013.01); *A61B 5/369* (2021.01); *G16H 15/00* (2018.01)

(58) Field of Classification Search
CPC ....... A61B 5/7275; A61B 5/369; G16H 15/00
See application file for complete search history.

(56) References Cited

U.S. PATENT DOCUMENTS

| 9,277,873 | B2 | 3/2016 | Sarma |
| 10,517,540 | B1 | 12/2019 | Anderson |
| 2016/0022193 | A1 | 1/2016 | Rau |
| 2017/0367607 | A1 | 12/2017 | Agarwal |
| 2022/0047204 | A1 | 2/2022 | Johannsson |
| 2022/0133194 | A1 | 5/2022 | Bach |

(Continued)

FOREIGN PATENT DOCUMENTS

| AU | 2021107413 A4 | 1/2022 | |
| WO | 2009103156 A1 | 8/2009 | |
| WO | WO-2009103156 A1 * | 8/2009 | ............... A61B 5/00 |

(Continued)

OTHER PUBLICATIONS

Xia et al., "Biomedical Signal Processing and Control," Biomedical Signal Processing and Control 46 (2018) 18-32; https://doi.org/10.1016/j.bspc.2018.06.004. Jul. 9, 2018.

(Continued)

*Primary Examiner* — Mohamed Charioui
*Assistant Examiner* — Christine Y Liao
(74) *Attorney, Agent, or Firm* — CUSPA Technology Law Associates; Yi Li

(57) ABSTRACT

A method and system for determining a treatment outcome prediction for a patient using electroencephalograph (EEG) are disclosed, which include analyzing a brain region mutual interaction characteristics using scalp EEG data from a patient and obtaining a set of brain region mutual interaction feature matrices, performing a feature enhancement process to the brain region mutual interaction feature matrices to extract prominent mutual interaction features and applying a treatment response predictive model to determine a treatment outcome prediction for the patient. Further disclosed is a method of generating a treatment response predictive model using EEG dataset of a group of patients under a clinical treatment. The method and system can be used for determining a treatment outcome prediction for a psychiatric disorder patient and a patient diagnosed with COVID-19 and suffering from psychiatric disorder symptom(s) originated from COVID-19.

19 Claims, 12 Drawing Sheets

(56) References Cited

U.S. PATENT DOCUMENTS

2022/0313140 A1\* 10/2022 Atasoy .................. G16H 40/63
2023/0092673 A1\* 3/2023 Mitrani .................. A61P 11/00
                                                         424/528

FOREIGN PATENT DOCUMENTS

| WO | 2010032929 A2 | 3/2010 |
| WO | 2020081609 A1 | 4/2020 |
| WO | WO-2021075548 A1 \* | 4/2021 |

OTHER PUBLICATIONS

TaghiBeyglou et al., "ADHD diagnosis in children using Common spatial pattern and Nonlinear Analysis of Filter banked EEG," 2020 28th Iranian Conference on Electrical Engineering (ICEE). (Year: 2020).

Al-Hadeethi et al., "An Eigenvalues-Based Covariance Matrix Bootstrap Model Integrated With Support Vector Machines for Multichannel EEG Signals Analysis," Front. Neuroinform. 15:808339; doi: 10.3389/fninf.2021.808339. Feb. 3, 2022.

Chai et al., "Classification of EEG based-Mental Fatigue using Principal Component Analysis and Bayesian Neural Network," 978-1-4577-0220-4/16/© 2016 IEEE, pp. 4654-4657. (Year: 2019).

Shi et al,. "Melancholia EEG classification based on CSSD and SVM," Proc. SPIE 8285, International Conference on Graphic and Image Processing (ICGIP 2011), 82854H (Oct. 1, 2011); doi: 10.1117/12.913271. Oct. 1, 2011.

Liu et al., "Review on Emotion Recognition Based on Electroencephalography," Front. Comput. Neurosci. 15:758212; doi: 10.3389/fncom.2021.758212. Oct. 1, 2021.

Clark et al., "Robust Assessment of EEG Connectivity Patterns in Mild Cognitive Impairment and Alzheimer's Disease," Front. Neuroimaging 1:924811; doi: 10.3389/fnimg.2022.924811. Jul. 11, 2022.

Shan et al., "Spatial-temporal graph convolutional network for Alzheimer classification based on brain functional connectivity imaging of electroencephalogram," Hum Brain Mapp. 2022;43:5194-5209; DOI: 10.1002/hbm.25994. Jun. 8, 2022.

Zhao et al., "Temporal and Spatial Dynamics of EEG Features in Female College Students with Subclinical Depression," Int. J. Environ. Res. Public Health 2022, 19, 1778. https://doi.org/10.3390/ijerph19031778. Feb. 4, 2022.

Michael X Cohen, "A tutorial on generalized eigendecomposition for denoising, contrast enhancement, and dimension reduction in multichannel electrophysiology," arXiv:2014.12356v3 [q-bio.QM] Jan. 28, 2022 (Year:2022).

Michael X Cohen, "Multivariate cross-frequency coupling via generalized eigendecomposition," eLife 2017;6:e21792. DOI: 10.7554/eLife.21792. (Year: 2017).

\* cited by examiner

METHOD AND SYSTEM FOR DETERMINING A TREATMENT OUTCOME PREDICTION FOR A PATIENT BASED ON ELECTROENCEPHALOGRAPH

FIELD OF THE INVENTION

The present invention relates to a method and system for determining a treatment outcome prediction for a patient using electroencephalograph, and further relates to a method of generating a treatment response predictive model using electroencephalograph.

BACKGROUND OF THE INVENTION

Psychiatric disorders impact a large number of people, such as major depression disorder (MDD), attention deficit and hyperactive disorder (ADHD), schizophrenia, Alzheimer's disease (AD), autism spectrum disorders (ASD), post-traumatic stress disorder (PTSD), etc. Psychiatric disorders are the number one reason for disability in the world, affecting nearly an estimated 970 million people in 2019 according to the World Health Organization (WHO).

A key issue in diagnosis and treatment of psychiatric disorders is the lack of physiological and pathological evidence. Diagnosis of psychiatric disorders still remains highly subjective. Today, the golden standards of diagnosis are heavily dependent on questionnaires filled by patients, their family and friends, and/or medical professionals after interactions with patients. For the same reasons, the current treatments are mainly based on trial-and-error approaches, in which medicine(s) or procedure(s) are prescribed based on certain subjective evidences and judgment calls. When the results of a clinical treatment are poor, another set of treatment may be prescribed, until some degree of success is achieved. Typically, patients have to try a number of clinical treatments before finding a suitable regiment. However, during such a process, patients suffer side effects of medicines and anxiety, and often lose confidence in the treatment, resulting further worsening of their conditions.

Due to the COVID-19 pandemic, the problems in diagnosis and treatment of psychiatric disorders are further exacerbated. On one hand, the prevalence of psychiatric disorders increased by 26% to 28%, according to WHO, mainly in anxiety and depression. On the other hand, the subjective diagnosis become more difficult and less accurate, due to lack of access to and interactions with medical professionals. It is also more difficult to the medical professionals to monitor treatment progress, which can result in severe consequences, such as suicide in major depression disorder patients.

Moreover, we now know that COVID-19 can also have longer-term effects. The term "long COVID" has been used to describe symptoms that continue after the initial acute infection period is over. Recently, WHO released a definition of a post-COVID condition which is helpful for promoting understanding and further research. Psychological aspects of post-COVID conditions involve post-COVID symptoms in the mental health. The most common symptoms include anxiety, depression or other mood changes, concentration or memory problems ("brain fog"), and sleep disturbance, as identified by U.S. Centers for Disease Control and Prevention (CDC).

One of the most informative studies to date is a study conducted by Jin Yin-tan Hospital in Wuhan, China and published in *The Lancet* in August 2021, in which the authors reported on one-year outcomes from the largest cohort of hospitalized adult COVID-19 survivors so far. They compared adult patients who had been hospitalized with COVID-19 to a group of age-matched adults living in the same community who had not had a COVID-19 infection. In one year, half of the infected patients had fully recovered, but the other half reported at least one continuing symptom. COVID-19 patients had more mobility problems, pain, anxiety, and depression than control participants. The study showed that many patients will not fully recover within a year of COVID-19 infection and that mental health symptoms are very significant.

Currently, doctors and scientists do not yet know what causes these distressing symptoms. There are several suggested possibilities for why they may occur. The long COVID symptoms could be the result of the specific effects of COVID-19 on the brain, the immune system, or other organ systems. Also, the long symptoms could be the result of traumatic aspects of the experience of having COVID-19. However, this explanation would not explain why severe mental health symptoms occur in people who were not seriously ill at the time of their initial COVID-19 infection. Ongoing psychological symptoms could also be the result of despair patients experience from long-term breathing problems or fatigue with no end in sight. Due to lack of understanding of the underlying cause for long COVID symptoms, currently there is no treatment guidelines for patients suffering from psychological symptoms from long term effects of COVID-19.

Scalp electroencephalography is a non-invasive method that uses an electronic monitoring device to measure and records an electrogram of the spontaneous electrical activity of the brain. Electroencephalograph (EEG) captures signals emitted by neurons in the human brain. These signals contain rich information about the brain activities and conditions. However, what electroencephalograph captures are collective electromagnetic signals emitted from millions or even billions of neurons performing very large number of tasks at the same time, it is practically impossible to interpret streams of signals directly by human eyes, except very few cases, such as epilepsy. Complex data processing and mathematical models need to be employed to discern meaningful information from the raw signals.

Due to the weakness of the signals captured by the electrodes, EEG signals in general have a low signal-to-noise ratio. Furthermore, due to the volume conduction effect, EEG signals are prone to be misinterpreted when inspecting differences between the signals of different electrodes. Due to the above reasons, existing analysis of EEG signals relies heavily on signal separation and statistical techniques. Technically, it has been difficult to directly use EEG data for assisting diagnosis and treatment of psychiatric disorder patients.

Recently, magnetic resonance imaging (MRI), either functional or structural, has been used to aid the analysis of EEG data, with different level of success. This approach, however, has some major drawbacks. First, MRI can induce new artifacts (distortion) into the analysis while mediating others. Using MRI also requires significant more computing power for the analysis. Second, using MRI data together with EEG data greatly increases the cost, complexity, and time requirement of data acquisition processes, hence limiting its clinical applications.

Therefore, there is a significant need for improved methods and systems that can effectively extract meaningful information from complex EEG signals and that can use extracted information for assisting diagnosis and treatment of psychiatric disorder patients. In particular, there is a significant need for improved methods and systems that can use EEG data to identify cohorts of psychiatric disorder patients, for example identifying a responsive cohort to a clinical treatment, and to determine a treatment outcome prediction for a patient. In this regard, there is a pressing need for identifying cohorts among long COVID or post-COVID condition patients who are likely suitable for certain existing clinical psychiatric/psychological treatments.

SUMMARY OF THE INVENTION

In one aspect, the present invention is directed to a computer-implemented method for determining a treatment outcome prediction for a patient using electroencephalograph. In some embodiments, the method includes receiving a scalp electroencephalograph (EEG) data from a patient; analyzing at least one type of brain region mutual interaction characteristics using the EEG data and obtaining a set of brain region mutual interaction feature matrices (MIFMs), each matrix for one frequency band of the EEG data; performing a multi-frequency band generalized eigenvalue decomposition (GED) process to the set of MIFMs to extract prominent mutual interaction features, thereby generating an eigenvector assembly matrix (EAM) of the patient; applying a treatment response predictive model to the eigenvector assembly matrix (EAM) and determining a treatment outcome prediction; and reporting the treatment outcome prediction for the patient.

In a further aspect, the present invention is directed to a method of generating a treatment response predictive model using electroencephalograph. In some embodiments, the method includes analyzing at least one type of brain region mutual interaction characteristics using a scalp electroencephalograph (EEG) data of each of a plurality of patients under a clinical treatment and obtaining a set of brain region mutual interaction feature matrices (MIFMs) of each patient, each matrix for one frequency band of the EEG data; performing a multi-frequency band generalized eigenvalue decomposition (GED) process to the set of brain region mutual interaction feature matrices (MIFMs) of each patient to extract prominent mutual interaction features, and generating an eigenvector assembly matrix (EAM) of each patient; and applying a machine learning algorithm to the eigenvector assembly matrix (EAM) from the plurality of patients, thereby generating a treatment response predictive model capable of determining a treatment outcome prediction of the clinical treatment using electroencephalograph.

In another, interrelated aspect, the present invention is directed to a system for determining a treatment outcome prediction for a patient using electroencephalograph. In some embodiments, the system includes at least one data processor; and at least one memory storing instructions which, when executed by the at least one data processor, result in operations including: analyzing at least one type of brain region mutual interaction characteristics using a scalp electroencephalograph (EEG) data from a patient and obtaining a set of brain region mutual interaction feature matrices (MIFMs), each matrix for one frequency band of the EEG data; performing a multi-frequency band generalized eigenvalue decomposition (GED) process to the set of MIFMs to extract prominent mutual interaction features, thereby generating an eigenvector assembly matrix (EAM); applying a treatment response predictive model to the eigenvector assembly matrix (EAM) and determining a treatment outcome prediction; and reporting the treatment outcome prediction for the patient.

The advantages of the present invention will become apparent from the following description taken in conjunction with the accompanying drawings showing exemplary embodiments of the invention.

BRIEF DESCRIPTION OF THE DRAWINGS

It is noted that in the drawings like numerals refer to like components.

DETAILED DESCRIPTION OF THE INVENTION

This application incorporates by reference a concurrently filed patent application entitled "Method and System for Identifying Cohorts of Psychiatric Disorder Patients Based on Electroencephalograph" in its entirety.

In one aspect, the present invention is directed to a novel method and system for identifying cohorts of psychiatric disorder patients based on scalp electroencephalograph.

As used herein, the psychiatric disorders include, but not limited to, major depression disorder (MDD), attention deficit and hyperactive disorder (ADHD), Schizophrenia, bipolar disorder, Alzheimer's disease (AD), autism spectrum disorders (ASD), post-traumatic stress disorder (PTSD), Parkinson's disease, anxiety, obsessive-compulsive disorder, eating disorder, stroke, and brain injuries. Some of these disorders are also considered as neurological disorders in the literature. For the purpose of the present invention, no distinction is made between psychiatric disorders and neurological disorders, since the method disclosed herein apply to all of these disorders. Moreover, herein the psychiatric disorder patients also include patients who have been diagnosed with COVID-19 and suffer from a psychiatric disorder symptom originated from COVID-19.

In electroencephalography measurement, a plurality of electrodes are placed along the scalp of a person, and the electroencephalograph (EEG) generated is commonly referred to as scalp electroencephalograph (scalp EEG) or scalp-recorded EEG. Herein, the term of EEG data refers to scalp EEG data of a person collected with an EEG device, which is also called EEG data sample interchangeably. In the present disclosure, the scalp EEG data can be received from a patient or from a healthy individual. Moreover, the EEG data or dataset in the processes described herein can involve healthy individuals.

The scalp EEG data can be collected in two different ways, resting state and event driven. With the resting state method, a subject is relaxed with a steady posture with either eyes-opened or eyes-closed, or alternate between opened and closed with known time intervals. The total recording is typically in the range of 10 to thousands of seconds. As an option, steady continuous stimuli can be given to the subject. The stimuli can be visual, audio, vibration, touch, olfactory, or anything that can cause neurological signals. With the event driven method, precisely timed stimuli are given to the subject, and instantaneous EEG responses are recorded and analyzed. The time period of interest is typically 0 to 2 seconds after a stimulus is given. Alternatively, the subject is asked to perform certain actions upon receive stimuli, such as press a key on a keyboard, click computer mouse, blink, or anything that represents a reaction to the stimuli. In some embodiments of the present invention, the resting state EGG data, with or without stimuli, is used.

Figure 3:
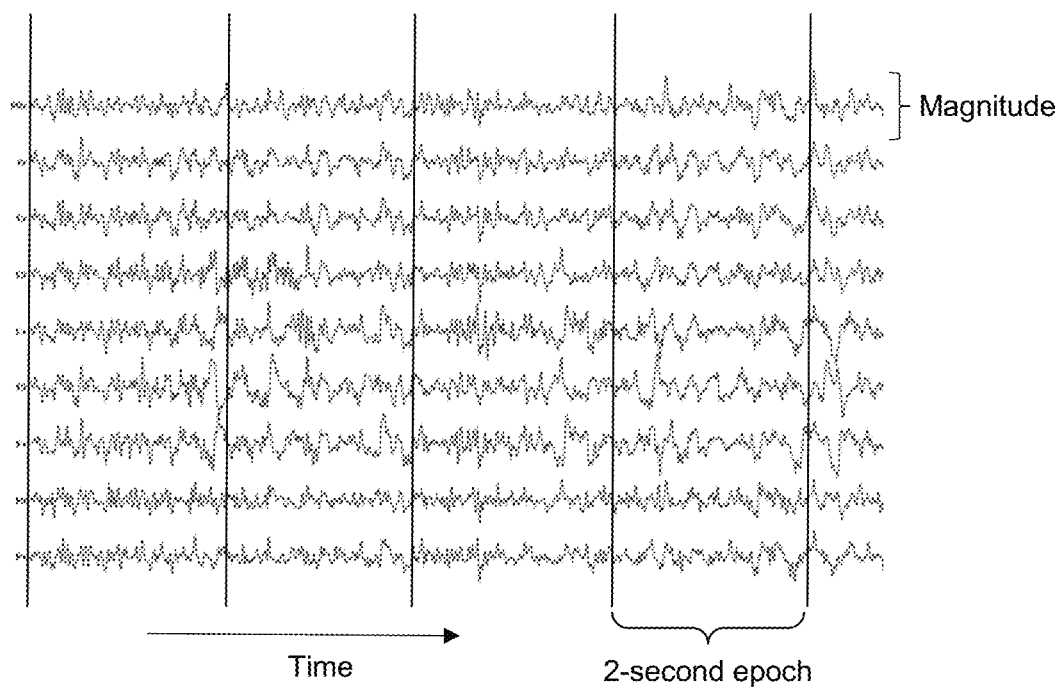
FIG. 3 shows a portion of a scalp EEG data with partitions of several epochs.

The scalp EEG captures signals emitted by neurons in the human brain. A scalp EEG device typically has a number of electrodes attached to human scalp with mechanical structure as support, or with adhesive or other means of attachment. The electrodes sense the analog electric signals emitted from neurons as the result of brain activities. Each electrode is connected directly or indirectly to an amplifier to amplify the signal to a level suitable for digitization. The electrodes are often referred to as channels. For an EEG device with N electrodes, the output is N time sequences of digitized signal waves. FIG. 3 shows a portion of an EEG data, where the horizontal axis is time, and the vertical axis is the magnitude of the signals. Each continuous trace of wave form is the signal of one electrode/channel. These signals contain rich information about the brain activities and conditions.

An EEG data sample received from a patient is typically from a few seconds to 10s of minutes long in term of the length of time. Given a T seconds long data and a digitalization sample rate S (namely, number of samples per second), data for one channel has K points, where $K=T \times S$, and the N-channel EEG data can be presented as a two dimensional matrix of N by K.

EEG signals are dynamic, meaning that the combination of the channel information varies as time passes. The dynamic nature causes the analysis of a sample with long time span to be ineffective, since important features can be "buried" in noises. In some embodiments, to overcome this problem, an EEG data is partitioned into small time segments, typically 2-4 seconds long, which are referred to as epochs. Therefore, a 60-seconds long EEG data sample can be partitioned into thirty 2-seconds long epochs, as illustrated in FIG. 3. As with any time continuous waveforms, EEG signals can be considered as a combination of many waveforms of different frequencies. At different frequency bands, an EEG data reveals different characteristics, therefore, analyses are often applied to selected frequency bands and/or combination of frequency bands.

Figure 1:
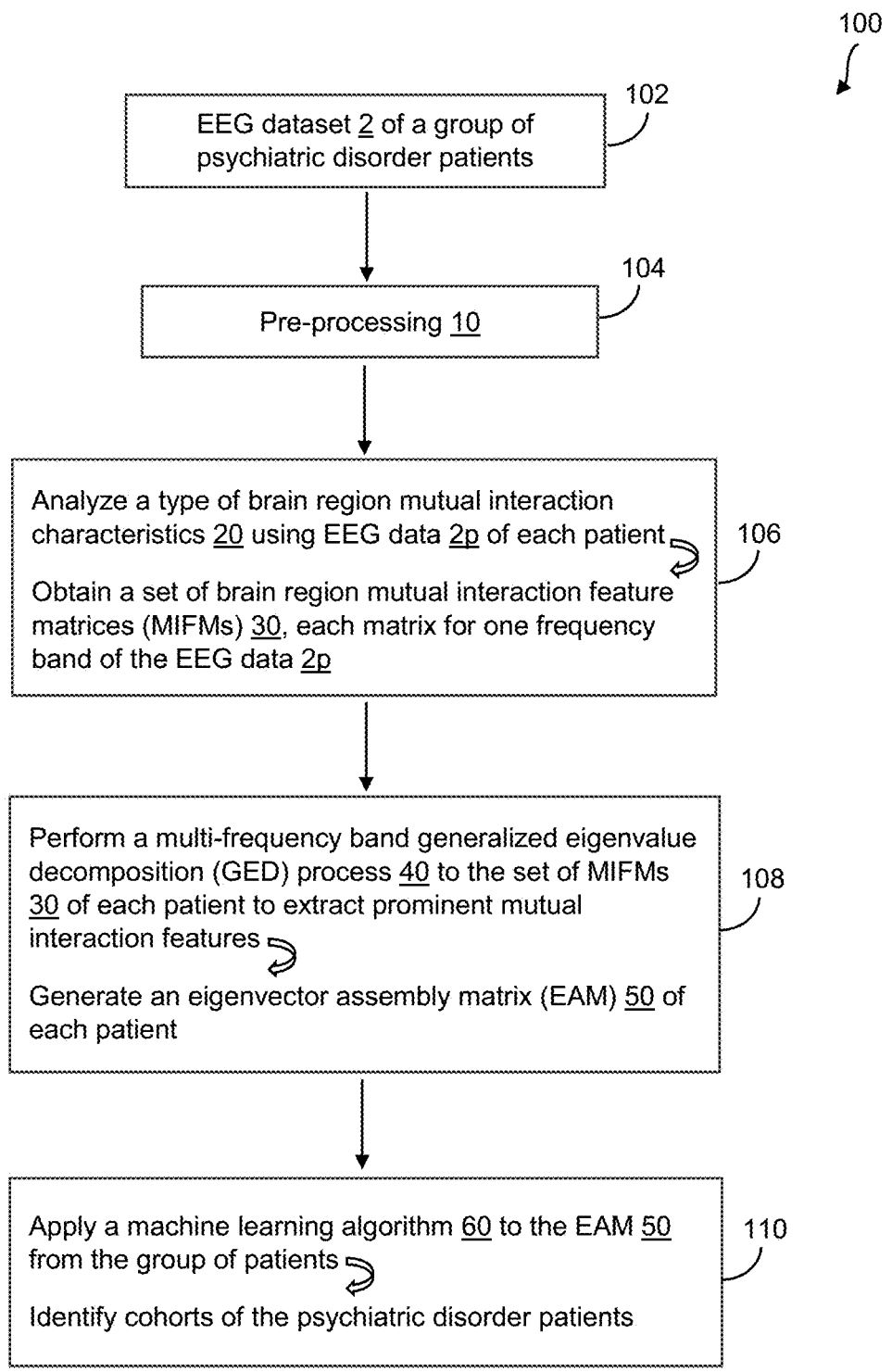
FIG. 1 is a flow diagram illustrating a method in one embodiment of the present invention.

In some embodiments, the present invention provides a computer-implemented method for identifying cohorts of psychiatric disorder patients using scalp EEG, as illustrated in FIG. 1. The method utilizes mutual interaction characteristics among brain regions as features for identifying cohorts. Brain regions can be described in different level of details. With the largest partition, a human brain can be divided into limbic system, frontal lobe, parietal lobe, occipital lobe, temporal lobe, and cerebellum. Each of these partitions can further contain different levels of detailed sub-partitions. Signals from an EEG electrode represent the regions under the electrode's surrounding areas. Herein, mutual interaction characteristics refer to discernable variation pattern(s) among the signals of two electrodes, therefore the brain regions represented by the two electrodes. Variation patterns of the signals between two electrodes can be characterized by different means, for example, by the extent to which their waveforms going positive or negative together in a certain form of synchronous manner, or by the Shannon information entropy changes that can be derived from the signals of the two electrodes, for each electrode as well as the relative changes of the two electrodes. The representative characterization is generally referred to as mutual interaction features.

As illustrated in FIG. 1, in an example process 100, an EEG dataset 2 (box 102) collected from a group of psychiatric disorder patients is used. Prior to analysis of a brain region mutual interaction characteristics, the raw EEG data of each patient received from an EEG device can be pre-processed or cleaned first by pre-processing 10 (box 104). In the raw EEG data, a channel with bad signals, for example, very high signal amplitudes or zero signal amplitudes, is interpolated by surrounding channels on the scalp. Too many bad channels, for instance 25% of all channels, will cause an EEG data to be discarded. During preprocessing, outliners are identified and eliminated. In some embodiments, the raw EEG data can be partitioned into a plurality of epochs, typically 2-4 seconds long. For an EEG data sample, its epochs may be compared with one and another, those epochs that are far different from others are discarded. As an example, epochs with an overall standard deviation of the signal amplitude higher than a predetermined threshold, such as certain times of the average standard deviation of all epochs, typically above three times, are discarded.

In the embodiment shown in FIG. 1, in the process 100 at least one type of brain region mutual interaction characteristics 20 is analyzed using a scalp EEG data 2p of each patient, which generates a set of brain region mutual interaction feature matrices (MIFMs) 30, in which each matrix is for one frequency band of the EEG data (box 106). Thereafter, a multi-frequency band generalized eigenvalue decomposition (GED) process 40 is carried out to the set of mutual interaction feature matrices 30 of each patient to extract prominent mutual interaction features. The GED process 40 generates an eigenvector assembly matrix (EAM) 50 of each patient (box 108). Subsequently, a machine learning algorithm 60 is applied to the eigenvector assembly matrix 50 from the group of psychiatric disorder patients, which identifies cohorts of the group of psychiatric disorder patients (box 110).

Herein, the types of brain region mutual interaction characteristics include, but not limited to, frequency band power, power-envelope correlation, coherence, weighted phase-lag index, imaginary part of coherence, covariance, mutual information, transfer entropy, and/or variants thereof. For example, coherence between all pairs of electrodes, or weighted phase lagging index between all pairs of electrodes can be analyzed. Herein, each type of the above mentioned mutual interaction characteristics, such as power-envelope correlation, coherence and their variants, has its ordinary meaning as established in the literature.

More specifically, in the process 100 at least one type of brain region mutual interaction characteristics is first analyzed using the preprocessed EEG data of each patient, which generates a set of brain region mutual interaction feature matrices (MIFMs) 30 for each patient, in which each matrix is for one frequency band of the EEG data (box 106). In an example embodiment, one type brain region mutual interaction characteristics is analyzed using an EEG data having a broadband range of 2-98 Hz. This broadband range can be partitioned into multiple narrowband ranges. For example, a narrowband can be 4 Hz wide, thus, Band1 through Band24 have frequency ranges (Hz), 2-6, 6-10, 10-14, . . . , 94-98. In this example, each matrix of the set of MIFMs 30 is for one narrowband. In another example, varying width among the narrowbands can be used.

Figure 4A:
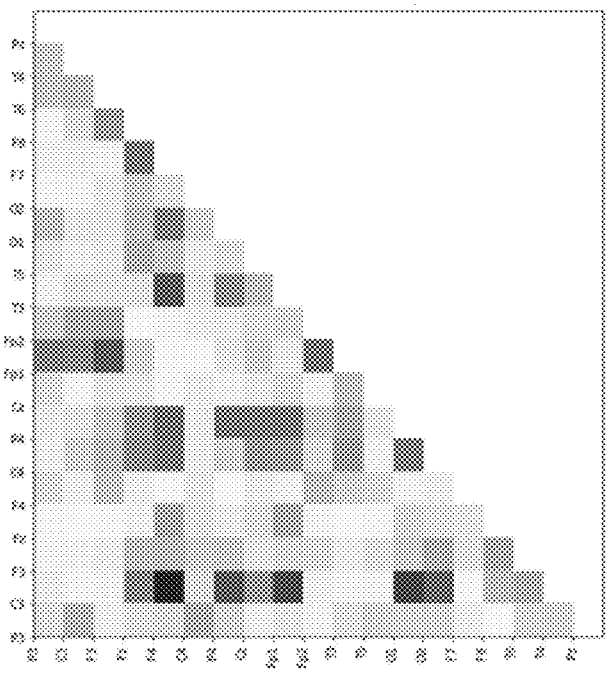
FIG. 4A shows a brain region mutual interaction feature matrix obtained in analysis of coherence of a scalp EEG data with the method in one embodiment of the present invention.

For an EEG device of N electrodes, there are $\frac{1}{2} \times (N \times N - N)$ pairs of electrodes. The pair-wise mutual interaction data are often represented as a triangular matrix, as illustrated in FIG. 4(A). In this example, the type of brain region mutual interaction characteristics analyzed is coherence. In this triangular matrix, the x-axis and y-axis are the same. Each point on an axis is the name of one electrode. Each cross point in the matrix is the mutual interaction data value of the brain region mutual interaction characteristics between two channels. The grayscale varies from white, as the lowest value, to black, as the highest value.

Figure 4B:
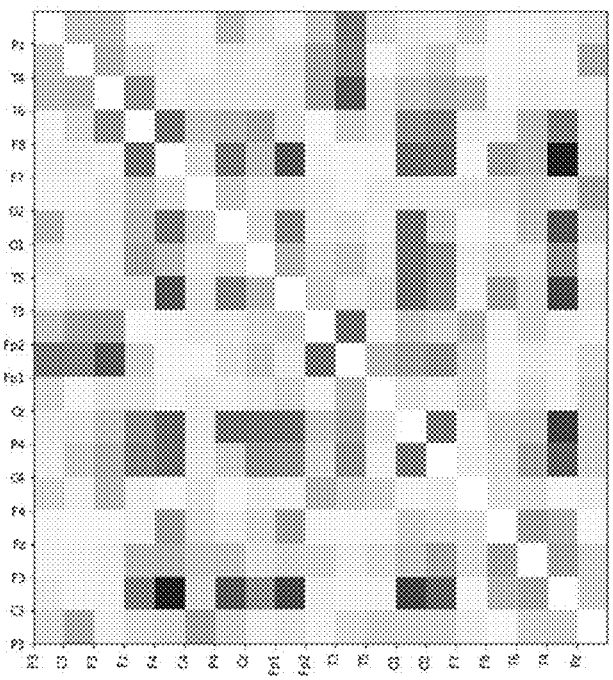
FIG. 4B shows the brain region mutual interaction feature matrix of FIG. 4A and its mirror image, displayed in the form of a square matrix.

For convenience, the triangular matrix is often displayed jointly with its mirror image in a form of a square matrix, as shown in FIG. 4(B). As can be readily appreciated, in the square matrix display, one can easily recognize mutual interactions of region from one electrode with all other electrodes in one straight row or column. More specifically, in FIG. 4(B) using electrode C3 on the Y-axis as an example, one can see along the X-axis, electrodes C3 and F4 have very high coherence, C3 and T5 have very low coherence, and C3 and F8 have a medium level of coherence.

In some embodiments, in analysis of certain types of brain region mutual interaction characteristics, further steps can be taken to reduce the effect of volume conduction. Volume conduction refers to the fact that the electrodes often receive signals from distant groups of neurons that are not directly in contact with the electrodes. Since volume conduction causes two electrodes to receive signals from the same sources, such signals can be mistakenly interpreted as synchronized activities between the two electrodes and the brain regions represented by the electrodes. By eliminating or reducing the effect of volume conduction, the independent signals of the two electrodes are clearly extracted. Several techniques can be employed to reduce the effect of volume conduction, which include, but not limited to, independent component analysis (ICA), contralateral difference (CD) and surface Laplacian (SL). In some embodiments, surface Laplacian is employed to reduce the effect of volume conduction. The surface Laplacian, also commonly referred to as current source density or scalp current density, and is a mathematical algorithm that transforms the scalp EEG data into estimates of radial current flow at scalp. The SL estimates have a sharper or more distinct topography, effectively reducing the negative impact of volume conduction, which may blur the scalp EEG signal. In this manner, surface Laplacian enhances the spatial resolution of the EEG signal, thus reduces the impact of volume conduction.

The above obtained brain region mutual interaction feature matrix 30 contain substantial information of brain activities. They can be used as direct inputs for machine learning algorithms to produce clustering or classification outputs. However, these brain region mutual interaction feature matrices typically have low signal-to-noise ratio, and generate poor results in identifying cohorts of patients with psychiatric disorders, as well as in determining treatment outcome prediction in further embodiments described below.

To extract meaningful information and suppress noise, a further feature enhancement process can be carried out to extract more representative and condensed information from the brain region mutual interaction feature matrices. The feature enhancement process may be accomplished using different techniques. In some embodiments, a generalized eigenvalue decomposition is used to extract the most representative information from brain region mutual interaction feature matrices as described in detail hereinafter. Alternatively, in some embodiments, the standard deviations of each row of the mutual interaction feature matrix 30 is calculated, which reflects the variation of the channel interaction between one respective channel and other channels. Then, a predetermined number of channels of the highest variation can be selected as a condensed version of the mutual interaction feature matrix for identifying cohorts of psychiatric disorder patients and for determining a treatment outcome prediction. In other alternative embodiments, a given subset of mutual interaction pairs can be selected based on known meaningful interaction pairs for certain psychiatric disorders as the inputs for identifying cohorts of psychiatric disorder patients and for determining treatment outcome prediction.

In the embodiment shown in FIG. 1, in process 100 after obtaining a set of brain region mutual interaction feature matrices 30, a multi-frequency band generalized eigenvalue decomposition (GED) process 40 is carried out to the set of mutual interaction feature matrices 30 of each patient to extract prominent mutual interaction features and suppress background noise (box 108).

The meaningful features of brainwaves are associated with various frequencies and the contrast between parameters of a narrow frequency band and the parameters of the broadband. In some embodiments, the GED process 40 utilizes a sequence of narrowband mutual interactions against the broadband mutual interactions as background to extract the most prominent vectors, as further described in detail below in reference to a multi-frequency band GED process in FIG. 2.

In some embodiments, each of the epochs of an EEG data is analyzed independently and a set of brain region mutual interaction feature matrices 30 of each epoch is generated. In the process 200 in FIG. 2, a multi-frequency band GED is first carried out to the set of mutual interaction feature matrices 30 of each epoch, which generates an eigenvector assembly matrix (eam-e) 50e of each epoch, see boxes 240-252. Thereafter, resulted eigenvector assembly matrix (eam-e) of all epochs are averaged to generate the eigenvector assembly matrix (EAM) of each patient.

More specifically, for each epoch, generalized eigenvalue decomposition is described as follows:

$$Ax = \lambda Bx$$

wherein A is the mutual interaction feature matrix of a narrowband frequency range and B is the broadband mutual interaction feature matrix. λ and x are eigenvalues and eigenvectors, respectively. A is a diagonal matrix, the i-th diagonal value corresponds to the eigenvector represented by the i-th column of x.

Using the same example of an EEG data having a broadband range of 2-98 Hz, which is partitioned into multiple narrowband ranges, each 4 Hz wide. Thus, Band1 through Band24 have frequency ranges (Hz), 2-6, 6-10, 10-14, . . . , 94-98. In this example, each matrix of the set of mutual interaction feature matrices 30 of each epoch is for one narrowband.

The broad frequency band mutual interaction is the mutual interaction feature matrix B generated with the wide frequency range, namely 2-98 Hz range. Each narrowband mutual interaction feature matrix A is the mutual interaction feature matrix of the i-th band. For each $A_i$, eigenvectors are computed as $$A_i x_i = \lambda B x_i$$

Let $v_i$ be the vector in $x_i$ with the largest eigenvalue. The $v_i$ represents the combination of channel features with the largest difference to the broadband mutual interaction matrix, in other words, represents prominent mutual interaction features (box 248).

Figure 2:
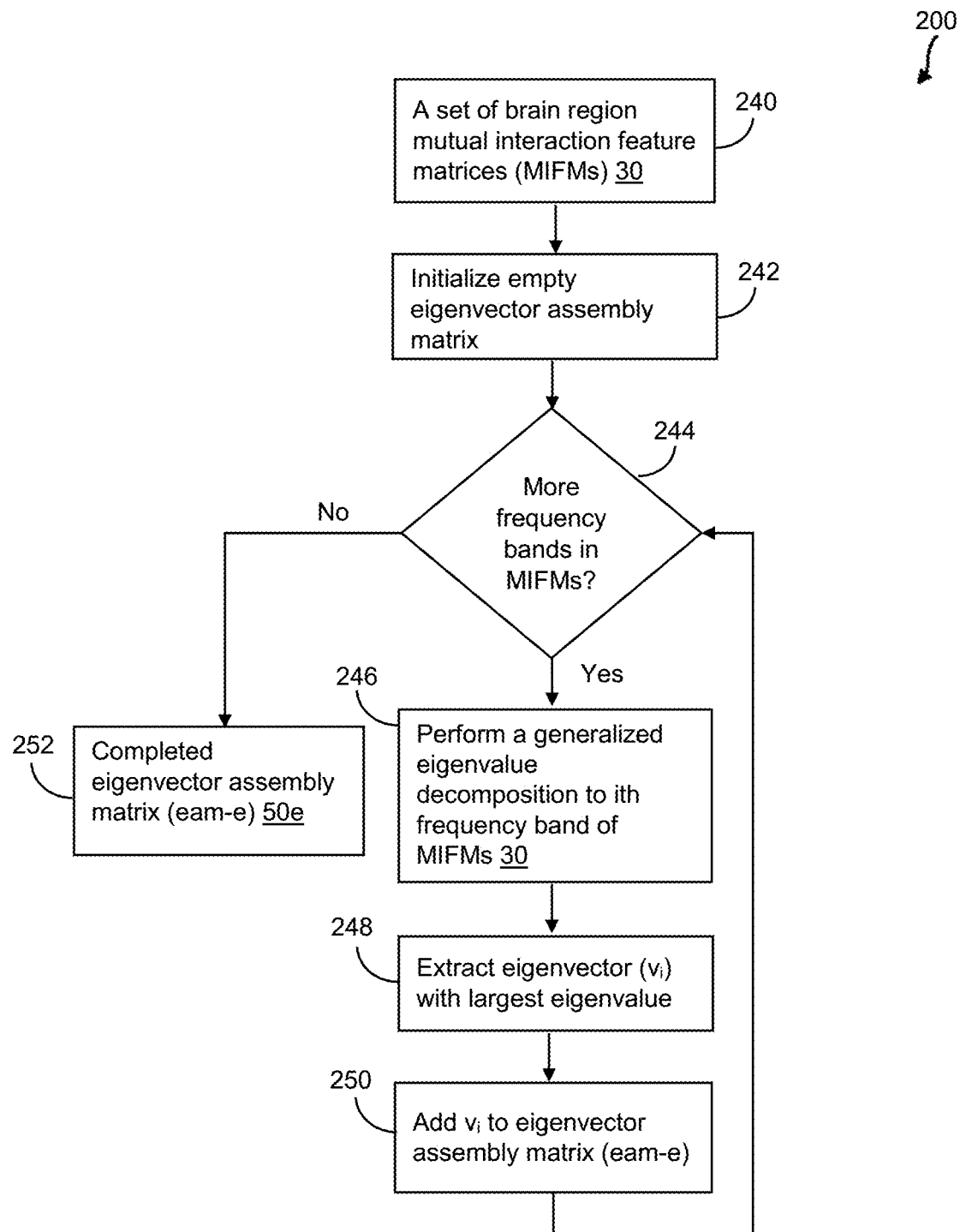
FIG. 2 is a flow diagram illustrating a multi-frequency band generalized eigenvalue decomposition process in one embodiment of the present invention.

As illustrated in FIG. 2, all $v_i$'s are put into a (number of frequency band)×(number of channels) eigenvector assembly matrix, eam-e, wherein the matrix (eam-e) contains prominent mutual interaction features of the epoch (boxes 250-252).

In the example process shown in FIG. 2, $v_i$ is the vector in $x_i$ with the largest eigenvalue. However, other vectors, such as the vectors in $x_i$ with the second or third largest eigenvalue, or the top 10 or 20 percent of eigenvalues, can also be used. In general, in the multi-frequency band GED process, the vectors with large eigenvalues represent the combination of channel features with large differences to the broadband mutual interaction matrix, and therefore, represent prominent mutual interaction features.

After obtaining the eigenvector assembly matrix (eam-e) 50*e* of all epochs, the matrices 50*e* of all epochs are averaged to reduce the noise introduced by dynamic changes along the timeline. The averaged result is denoted as an eigenvector assembly matrix (EAM) of a patient, which represents an electro-physiological profile or a brain activity digital profile of the patient.

Moreover, before averaging the eigenvector assembly matrices 50*e* of all epochs, if one or more matrices 50*e* are substantially different from the others, these outliers are eliminated. The determination of outliers and elimination can be carried out by various methods. In one exemplary embodiment, Euclidean distance is used for elimination before averaging the matrices 50*e* of all epochs. Commonly, using Euclidean distance, three times beyond average is used as a predetermined threshold to identify outliers. However, other feasible predetermined thresholds for defining outliers, depending on the specific types of brain region mutual interaction characteristics being analyzed, can also be used.

In an alternative embodiment, the eigenvector assembly matrix 50 of a patient can also be obtained by performing a multi-frequency band generalized eigenvalue decomposition process to the set of brain region mutual interaction feature matrices 30 of each patient, which are generated by analyzing a type of brain region mutual interaction characteristics of the entire EEG data without segmenting the EEG data to a plurality of epochs.

After obtaining the eigenvector assembly matrix 50 for each of a group of patients with psychiatric disorders in either manner as described above, a machine learning algorithm 60 is applied to the eigenvector assembly matrices 50 of the group to identify cohorts of the group of psychiatric disorder patients.

Herein, the cohorts of psychiatric disorder patients include responsive and non-responsive groups to a clinical treatment, different treatment outcome groups in response to a clinical treatment, as well as different risk types to a clinical treatment. Herein, the term of clinical treatment includes a treatment with one or more medications, treatment with one or more clinical procedures, for example psychotherapy, somatic therapy and the like, or treatment with combination of procedure(s) and medication(s).

In some embodiments, the machine learning algorithm 60 can be a clustering or classification algorithm for separating patients into cohorts. Suitable examples of clustering or classification algorithm include K-means, Gaussian Mixture Model (GMM), Balance Iterative Reducing and Clustering using Hierarchies (BIRCH), Affinity Propagation, Density-based Spatial Clustering of Applications with Noise (DBSCAN), and others. Furthermore, before a clustering or classification algorithm is applied, optionally the dimension of the data can be reduced, so that the clustering or classification algorithm can generate more meaningful data, as well as can operate more efficiently. For example, a principle components analysis (PCA) algorithm can be applied to reduce the dimension of the data. Alternatively, truncated singular value decomposition (Truncated SVD) or Autoencoder can also be used.

Moreover, in some embodiments, optionally a feature selection algorithm may be applied before the machine learning algorithm is applied to the eigenvector assembly matrices 50 of a group of patients to reduce the number of features as inputs to the machine learning algorithm. The feature selection algorithm selects only the most meaningful features as inputs to the machine learning algorithms. Such reduction of the number of input features facilitates the machine learning algorithms in producing clearer results, as well as operating more efficient. One suitable example of the feature selection algorithm is recursive feature elimination.

In some embodiments, the above described method can be used for evaluation of clinical trial results and for resolving deficiencies in current clinical trials that involve psychiatric disorders. In a clinical trial for a new medicine, patients are usually divided into at least two randomly assigned groups, a "treatment group" and a "placebo group". The treatment group is administered the medicine of the clinical trial for treatment of a targeted disease, and the placebo group is given placebo, which means no treatment of the targeted disease is given. The clinical trial outcomes of the two groups are compared to assess the effectiveness of the medicine in treating the disease. However, because of the often-high response rate to placebo in psychiatric disorder treatment trials, often the true effect of the treatment is "buried" and no statistically significant result is observed. Furthermore, most psychiatric disorder diagnosis relies heavily, if not exclusively, on subjective evaluations, such as patient self-reporting questionnaires, family member or friend questionnaires, or questionnaires filled by medical professionals based on their observations. Due to the subjectiveness nature of the psychiatric disorder diagnosis, patients with different underlying neurological or psychological conditions are often mixed together. For example, patients with symptoms caused by underlying neurological disorders and patients with symptoms caused by other factors other than the neurological disorders of interest may both participate in a clinical trial. Often, patients without underlying neurological disorders tend to respond to placebos well. Therefore, when these two types of patients are mixed into one trial group, the effects of the new medicine under the trial may not be correctly recognized. This may lead to a "failure" outcome of the clinical trial, and consequently, a misperceived failure of the new medicine. Such misperceived failures can cause millions or even billions of dollars to pharmaceutical companies involved in developing new medicines, and setbacks in offering potential new medical treatments to the patients.

With the method of the present invention, patients with certain underlying neurological disorders can be effectively separated from those without the neurological disorders or those with other type of disorders. Therefore, the real effect of the medicine under clinical trial can be accurately recognized with demonstrable statistical significance and effect size.

In further embodiments, the present method may further include analyzing one or more other types of brain region mutual interaction characteristics and combining the information from different types of brain region mutual interaction characteristics for cohort identification among psychiatric disorder patients, as well as for determining a treatment outcome prediction for a patient as described hereinafter.

Figure 5:
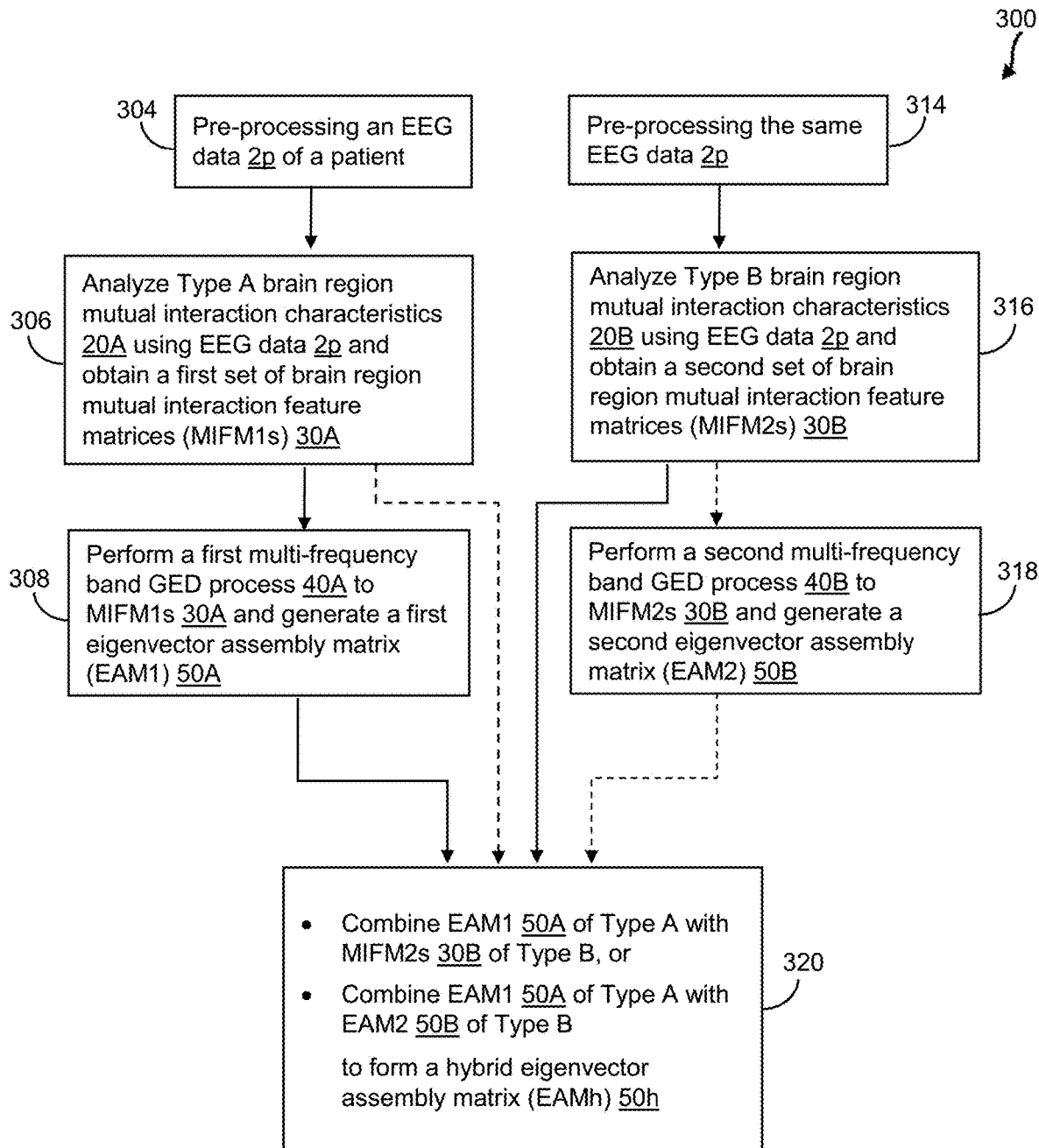
FIG. 5 is a flow diagram illustrating a process in generating a hybrid eigenvector assembly matrix in an example embodiment of the present invention.

More specifically, as illustrated in FIG. 5, in an example process 300, a first type brain region mutual interaction characteristics (Type A) 20A is analyzed using a scalp EEG data 2p of a patient in the manner described above, which generates in a first set of brain region mutual interaction feature matrices (MIFM1s) 30A. Thereafter, in the same manner described above, a first multi-frequency band GED process 40A is performed to the first set of MIFM1s 30A to extract prominent mutual interaction features, which generates a first eigenvector assembly matrix (EAM1) 50A of the patient, see boxes 304-308.

Then, as further shown on the right side in FIG. 5 (boxes 314-318), a second type brain region mutual interaction characteristics (Type B) 20B is analyzed using the EEG data 2p of the same patient, which generates a second set of brain region mutual interaction feature matrices (MIFM2s) 30B. In the same manner described above, a second multi-frequency band GED process 40B can also be performed to the second set of mutual interaction feature matrices 30B, which generates the second eigenvector assembly matrix (EAM2) 50B of the patient, see box 318.

Thereafter, as shown in FIG. 5 (box 320), the matrices obtained on both left and right sides can be combined in several different manners. In some embodiments, the first eigenvector assembly matrix 50A can be combined with the second set of mutual interaction feature matrices 30B, or with the second eigenvector assembly matrix 50B, to form a hybrid eigenvector assembly matrix (EAMh) 50h for the patient. Similarly, the second eigenvector assembly matrix 50B can be combined with the first set of mutual interaction feature matrices 30A, or with the first eigenvector assembly matrix 50A, to form a hybrid eigenvector assembly matrix 50h for the patient.

In the embodiments illustrated in FIG. 5, the hybrid eigenvector assembly matrix 50h provides a further enhanced human brain activity digital profile that strengthens electro-physiological characteristics of the patient. With the enhanced human brain activity digital profiles of a group of psychiatric disorder patients, the ability of the above described method in identifying cohorts of psychiatric disorder patients, as well as the ability in determining treatment outcome prediction for a patient in a process described hereinafter, can be further enhanced. Moreover, the enhanced human brain activity digital profiles established from a large group of psychiatric disorder patients can also be used in assisting diagnosis of psychiatric disorders.

In some embodiments, a hybrid eigenvector assembly matrix 50h obtained in the process 300 is used for identifying cohorts of psychiatric disorder patients. More specifically, same as in the process 100 described above in reference to FIG. 1, a machine learning algorithm 60 is applied to the hybrid eigenvector assembly matrices 50h obtained from a group of psychiatric disorder patients to identify cohorts of the group of patients. In other embodiments, the hybrid eigenvector assembly matrices 50h obtained from a large group of patients is used for generating a machine learning model for predicting treatment outcome as further described hereinafter.

In an exemplary embodiment, the first type brain region mutual interaction characteristics is coherence and the second type brain region mutual interaction characteristics is a power-envelope correlation. In this example, the first eigenvector assembly matrix (EAM1) obtained from analysis of coherence of EEG data of a patient can be combined either with the second set of brain region mutual interaction feature matrices (MIFM2s) or with second eigenvector assembly matrix (EAM2) obtained from analysis of the power-envelope correlation of the EEG data of the same patient to generate a hybrid eigenvector assembly matrix.

The manner of combining matrices obtained from the analyses of different types of brain region mutual interaction characteristics may depend on the specific machine learning algorithm used in identifying cohorts of psychiatric disorder patients or in generating the treatment response predictive model for determining treatment outcome prediction, or a diagnostic model for diagnosis of a disease as described hereinafter. A typical combination can be carried out by flattening the two matrices obtained from two types of brain region mutual interaction characteristics to two 1-dimensional matrices, and then concatenating the two 1-dimensional matrices with assigned weights for each of them. For example, one matrix may have a weight of 0.7 and another matrix may have a weight of 0.3. Other suitable methods for combining matrices can also be used. As an example, the common dimension of two mutual interaction feature matrices can be concatenated to form a hybrid 2-dimensional matrix. Such a common dimension can be channels or frequency bands. Furthermore, elements of the matrices can be selected to form a new 1-dimensional matrix based on most significant mutual interaction pairs developed through study.

The effectiveness of the present method in identifying different cohorts of psychiatric disorder patients is demonstrated in an example below. In this example, the results of a previous clinical trial for an anti-depression drug as evaluated based on reduction of HAM-D scores (Hamilton rating scale for depression) during the treatment failed to show the effect of the anti-depression drug among the participating patients who were diagnosed with major depressive disorder. The method described above in reference to FIGS. 1, 2 and 5 was used to evaluate the trial results by analyzing scalp EEG dataset of the participating patients, which resulted in a clear identification of two distinctly different cohorts: responsive cohort (Cohort 1) and non-responsive cohort (Cohort 2).

Figure 14:
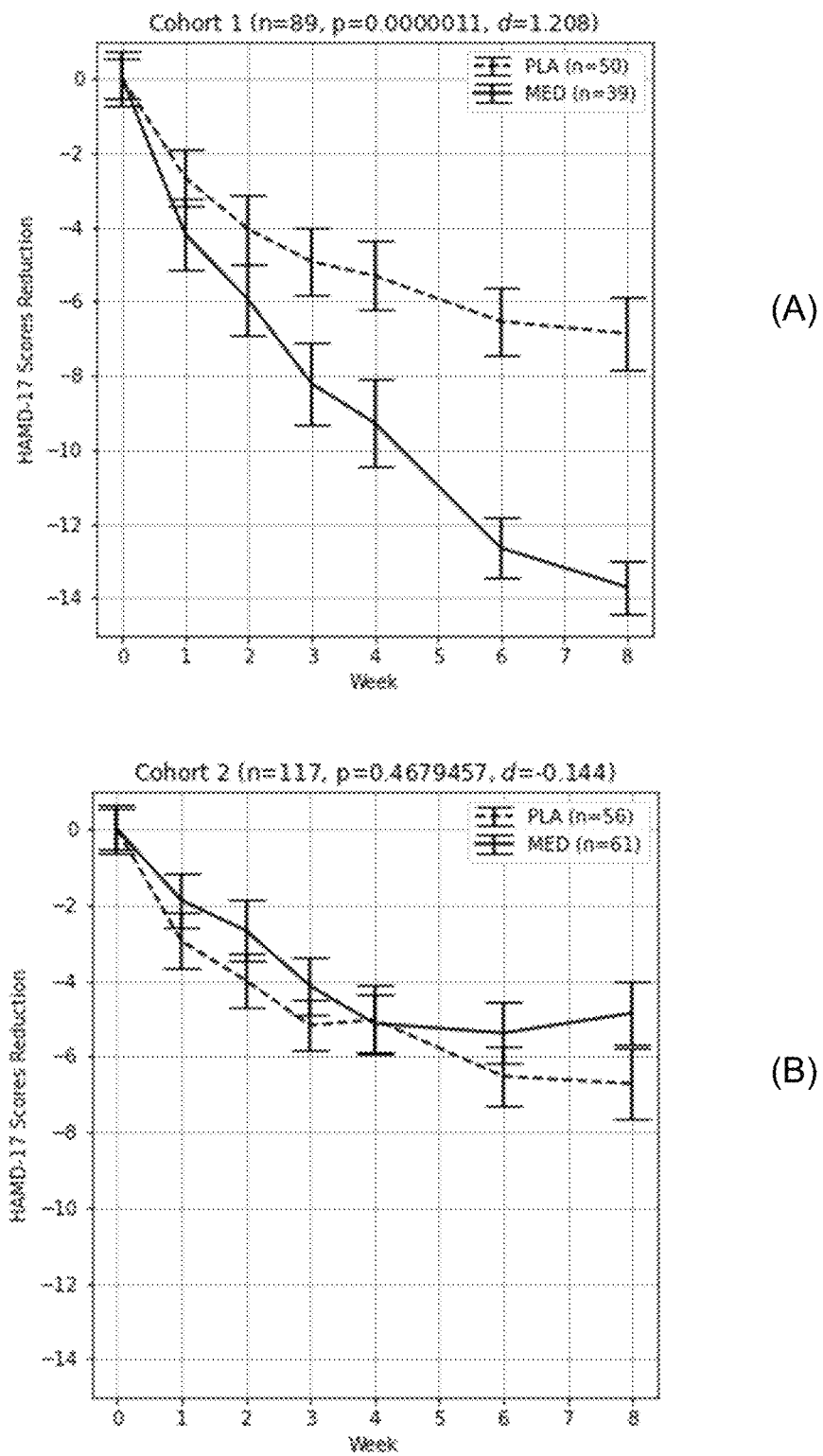
FIG. 14 shows the results of identifying responsive and non-responsive cohorts of the participating patients in the clinical trial using the method in an example embodiment of the present invention.

As described in the example and shown in FIG. 14(A), in Cohort 1 the treatment group exhibited a drastic reduction of HAM-D scores in response to the anti-depression drug treatment, with statistically significant difference from the placebo group (p=0.0000011) and a large effect size (d=1.208). On the contrary, Cohort 2 patients showed no difference between the treatment group and placebo group (p=0.4679457) and a negative effect size (indicating the treatment group had worse response than the placebo group), see FIG. 14(B). Therefore, in this example the method described above successfully revealed that the anti-depression drug was effective for an identifiable patient population of major depressive disorder patients, and the drug could be specifically purposed for this patient population. This is a situation analogous to existing diabetes drugs that are effective in treating Type-2 diabetes patient population, but not effective to all types of diabetes patient populations.

Therefore, the present method can be used to improve quality and effectiveness of clinical trials for treating psychiatric disorder patients, and to avoid often ill-concluded trial failures. In this example, without using the method of the present invention, the efficacy of the anti-depression drug to a specific population of major depressive disorder patients would not be revealed. Moreover, the result of identifying this patient population (Cohort 1) will also lead to further research on the underlying neurological and psychological conditions of this population, which will improve future diagnosis and treatment of these patients.

In addition, in some embodiments the present method can also be further combined with other types of clinical data to form multimodal methods. For example, the method described above can be further combined with known rating scale questionnaires, genetic information, blood test results, etc., to form multimodal solutions which could further enhance accuracy or effect size of the present method with additional corroborating information.

Moreover, in some further embodiments, the first set of mutual interaction feature matrices 30A and the second set of mutual interaction feature matrices 30B shown in FIG. 5 can be combined to form a hybrid feature matrix. By combining two set of mutual interaction feature matrices together, the hybrid feature matrix enhances extraction of meaningful brain region mutual interaction features. The hybrid feature matrix can be used in the same manner as the hybrid eigenvector assembly matrix for identifying cohorts, as well as for determining a treatment outcome prediction.

In a further aspect, the present invention further provides a method for determining a treatment outcome prediction for a patient. Herein, the term of treatment outcome refers to responsiveness to a clinical treatment, different levels of treatment result, different levels of risk to a clinical treatment, or other known criteria associated with evaluating medical treatment.

Figure 6:
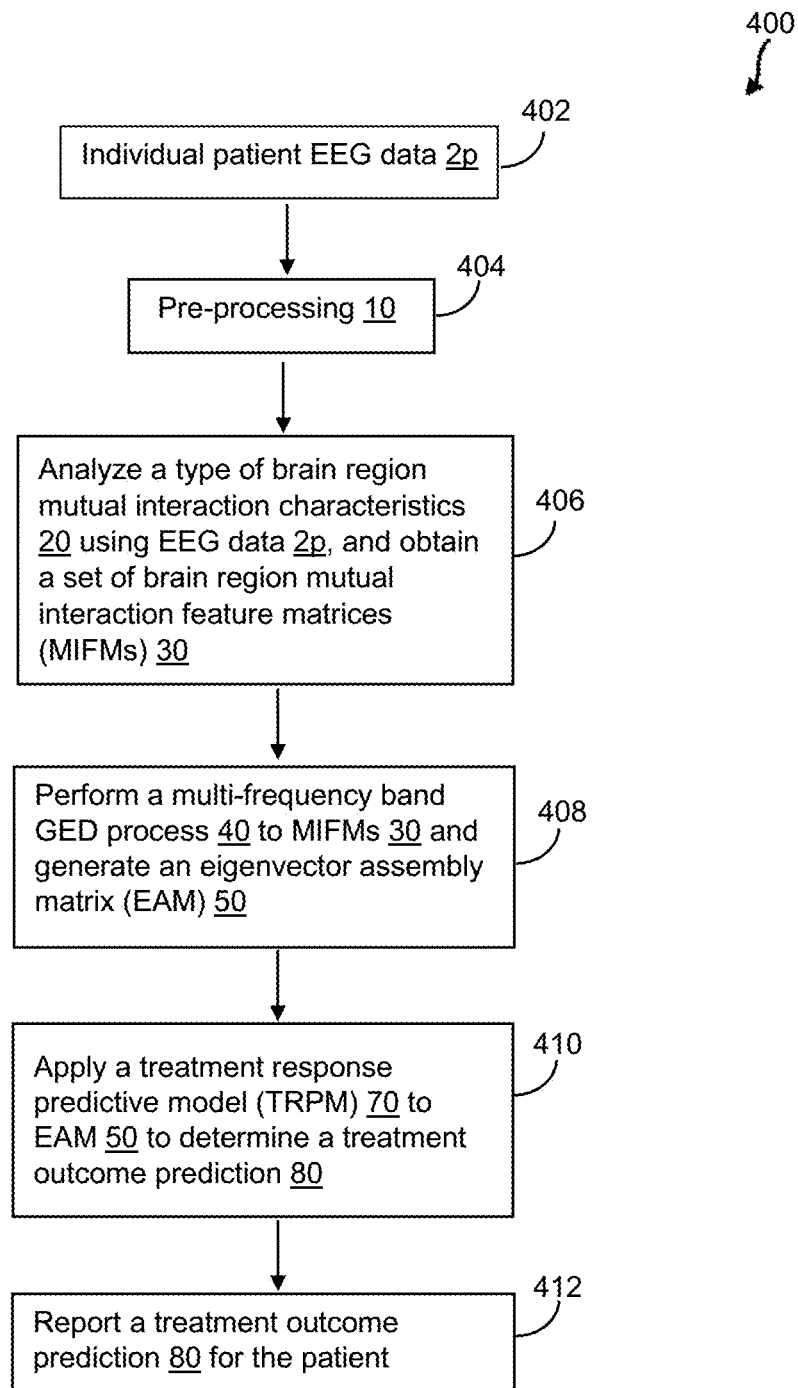
FIG. 6 is a flow diagram illustrating a process of determining a treatment outcome prediction for a patient in one embodiment of the present invention.

In some embodiments, the method for determining a treatment outcome prediction for a patient can be carried out in a process 400 illustrated in FIG. 6. As shown in process 400, after receiving a scalp EEG data sample 2p from a patient, at least one type brain region mutual interaction characteristics is analyzed after preprocessing, which generates a set of brain region mutual interaction feature matrices (MIFMs) 30, in the same manner described above, in which each matrix is for one frequency band of the EEG data (boxes 402-406). Thereafter, a multi-frequency band GED process 40 is performed to the set of mutual interaction feature matrices 30 to extract prominent mutual interaction features, which generates an eigenvector assembly matrix (EAM) 50 of the patient (box 408), in the same manner described above in reference to FIGS. 1 and 2. Subsequently, a treatment response predictive model (TRPM) 70 is applied to the eigenvector assembly matrix 50 to determine a treatment outcome prediction for the patient (boxes 410-412).

Figure 7:
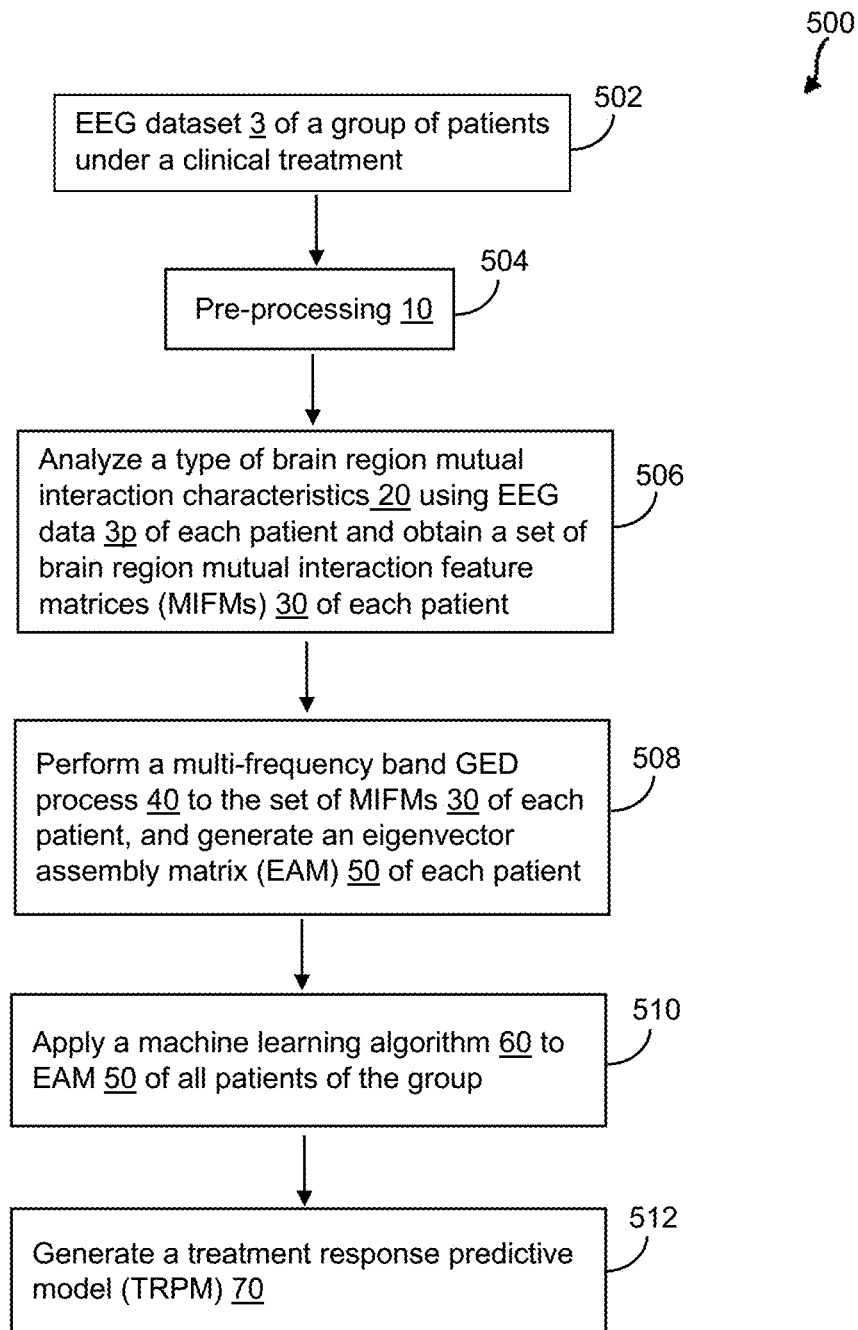
FIG. 7 is a flow diagram illustrating a process of generating a treatment response predictive model in one embodiment of the present invention.

In a further aspect, the present invention provides a method of generating a treatment response predictive model. In generating the treatment response predictive model, an EEG dataset obtained from a group of patients under a clinical treatment is used. FIG. 7 illustrates an example process 500 for generating the treatment response predictive model 70 in some embodiments.

As shown, in the process 500, the process steps in boxes 502-508 used to generate the treatment response predictive model 70 are the same as those corresponding steps in the process 100 for identifying cohorts of patients described above in reference to FIGS. 1 and 2. More specifically, in the process 500, after preprocessing an EEG dataset 3 from a group of patients under a clinical treatment, at least one type of brain region mutual interaction characteristics is analyzed using EEG data 3p of each patient, in the same manner described above, which generates a set of brain region mutual interaction feature matrices (MIFMs) 30 of each patient, in which each matrix is for one frequency band of the EEG data (boxes 502-506). Thereafter, a multi-frequency band GED process 40 is performed to the set of mutual interaction feature matrices 30 of each patient to extract prominent mutual interaction features, which generates an eigenvector assembly matrix (EAM) 50 for each patient (box 508), in the same manner described above. Subsequently, a machine learning algorithm 60 is applied to the eigenvector assembly matrices 50 from all patients of the group, which generates a treatment response predictive model 70 that is capable of determining a treatment outcome prediction based on EEG data of a patient (boxes 510-512).

In the process 500, the treatment response predictive model 70 is trained with sufficient data from patients under a clinical treatment, therefore, the model can distinguish features or patterns of the patients who are responsive to the treatment and those who are not responsive to the treatment. Therefore, the treatment response predictive model 70 generated can predict a treatment outcome of the clinical treatment for a patient using the patient's EEG data with the process 400 described above.

Figure 8:
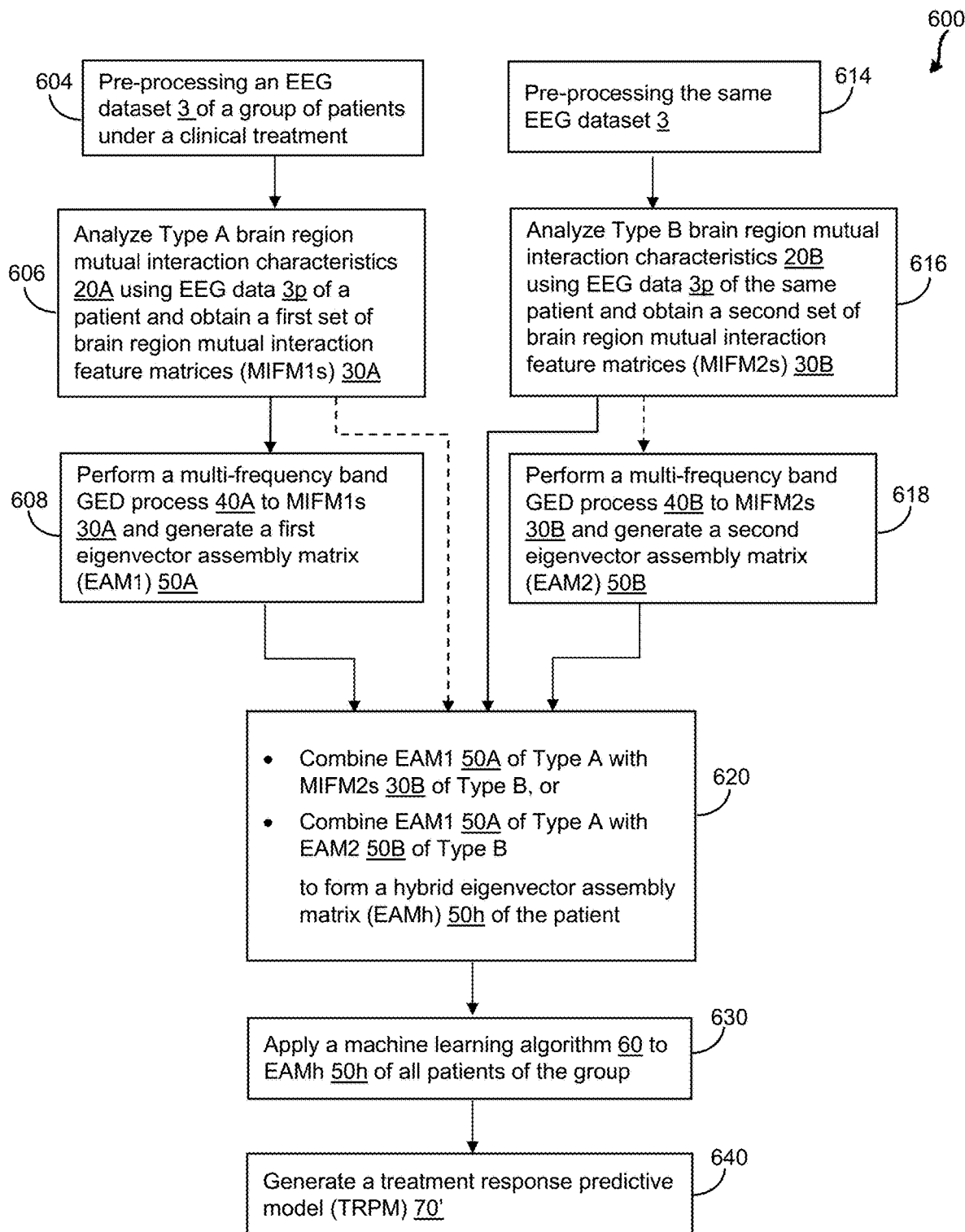
FIG. 8 is a flow diagram illustrating a process of generating a treatment response predictive model in a further embodiment of the present invention.

FIG. 8 further illustrates another example process for generating a treatment response predictive model 70' in some embodiments. As shown, in the process 600 the steps shown in boxes 604-608, 614-618 and 620 used to generate the treatment response predictive model 70' are the same as corresponding steps in process 300 used to form a hybrid eigenvector assembly matrix (EAMh) 50$h$ of a patient, which are performed in the same manner described above in reference to FIG. 5. However, as shown, in the process 600 for generating the treatment response predictive model, an EEG dataset 3 obtained from a group of patients under a clinical treatment is used, wherein the EEG data of an individual patient under the treatment is designated as 3p. In the process 600, after obtaining the hybrid eigenvector assembly matrix (EAMh) 50$h$ of each patient, a machine learning algorithm 60 is applied to the hybrid eigenvector assembly matrix 50h of all patients of the group, which generates the treatment response predictive model 70' (boxes 630-640).

Figure 9:
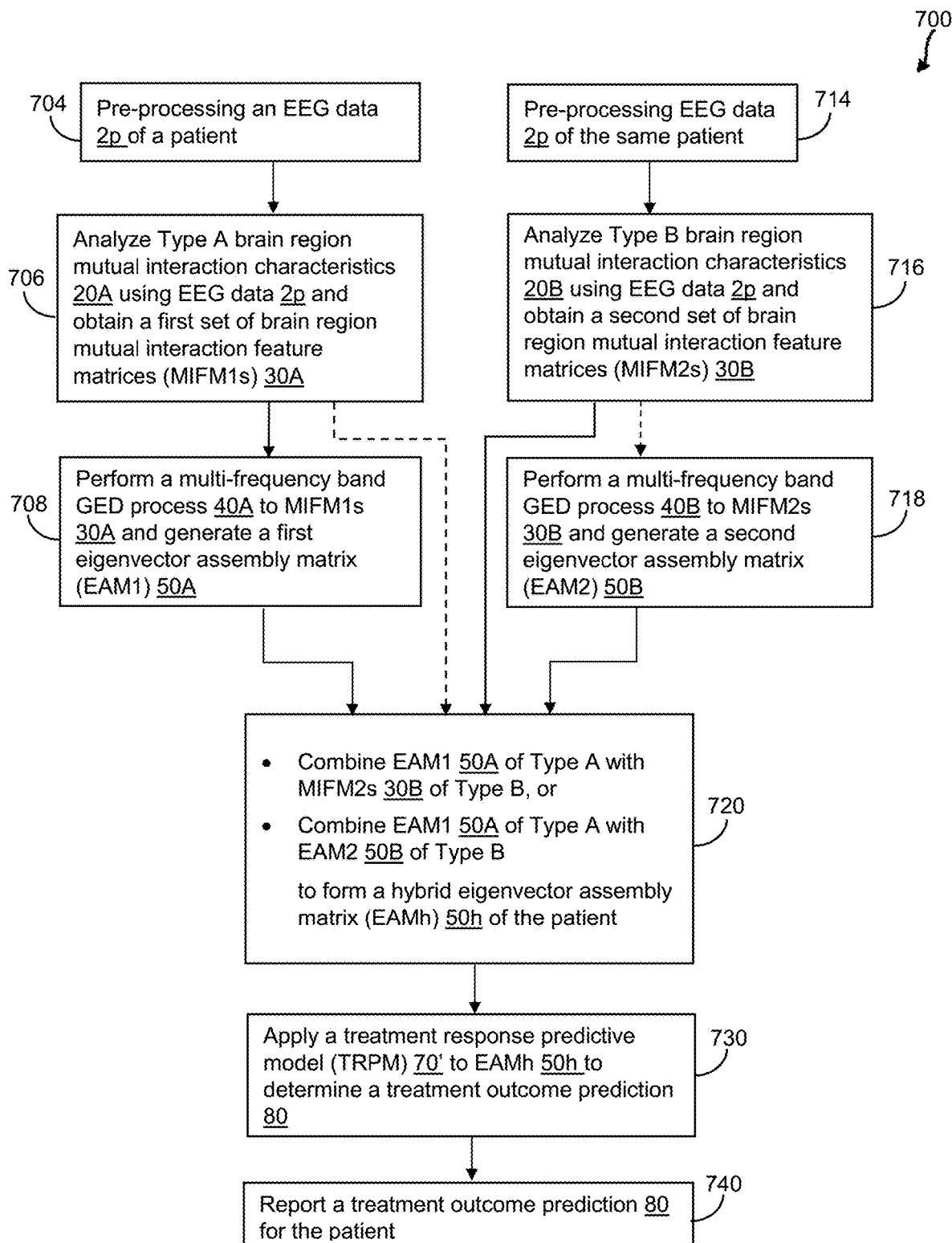
FIG. 9 is a flow diagram illustrating a process of determining a treatment outcome prediction using the treatment response predictive model generated in the process shown in FIG. 8.

In some embodiments, the treatment response predictive model 70' obtained in the process shown in FIG. 8 is used to determine a treatment outcome prediction for a patient as illustrated in FIG. 9. As shown in an example process 700 in FIG. 9, the process steps shown in boxes 704-708, 714-718 and 720 are the same as the corresponding steps in process 300 used to form a hybrid eigenvector assembly matrix (EAMh) 50h of a patient, which are performed in the same manner described above in reference to FIG. 5. Subsequently, after obtaining the hybrid eigenvector assembly matrix 50h from the patient, the treatment response predictive model 70' is applied to the hybrid eigenvector assembly matrix 50h to produce a treatment outcome prediction 80 for the patient (boxes 730-740).

When the above described process 500/600 is, respectively, built into a machine learning model with sufficient data for a particular clinical treatment for treating a disease, the machine learning model can be used for clinical prescription guidance. For example, patients who are determined as responsive subjects by the process 400/700 using the respective treatment response predictive model 70/70' will have good response to a clinical treatment, such as a medicine or a procedure, with high probability, whereas those determined as non-responsive subjects will have a low success probability. Therefore, the present method reduces the need for using a trial-and-error approach to treat patients with a potential medication, thus effectively reduces unnecessary suffering and side effects of the medication to some patients.

In some exemplary embodiments, the above described method can be used to determine a treatment outcome prediction of a clinical treatment for psychiatric disorder patients. Moreover, in some exemplary embodiments, the above described method can be particularly beneficial for patients suffering from psychiatric disorder symptoms originated from COVID-19, such as post-COVID conditions like anxiety, depression, mood changes, concentration or memory problems (brain fog). The above described method can be used to assess a treatment outcome prediction of existing psychiatric disorder clinical treatment(s) for long COVID patients. In addition, scalp EEG is broadly used in assessing or monitoring brain injuries due to trauma. In some embodiments, the above described method can be used to assess a treatment outcome prediction of available clinical treatment(s) for brain injury patients.

Moreover, in some further embodiments, in the above described process of generating a model such as in the manner of process 500/600, the EEG dataset can include EEG data from patients diagnosed with a disease and from healthy individuals. When the machine learning model is trained with sufficient data from both populations, the model can distinguish abnormal and normal features or patterns, and therefore can be used for clinical diagnosis, such as diagnosis of certain psychiatric disorders or certain brain injuries. Therefore, using an EEG dataset including both healthy individuals and patients diagnosed with a disease, the above described method generates a diagnostic model for clinical diagnosis.

In an exemplary embodiment, EEG data is acquired from each of a group of patients having post-COVID conditions involving one or more psychiatric disorder symptoms, as well as from each of a group of healthy individuals who are not infected by COVID-19 and do not have the one or more psychiatric disorder symptoms. The process 100, 200 and 300 described above in reference to FIGS. 1, 2 and 3 can be used with such an EEG dataset to differentiate normal and abnormal cohorts. Moreover, the process 500 or 600 described above in reference FIGS. 7 and 8 can be used with such an EEG dataset for generating a diagnostic model with a capability of distinguishing certain post-COVID condition patients. The diagnostic model can be used for identifying certain post-COVID condition patients using EEG. This will facilitate research and understanding of related post-COVID conditions and development of treatments.

In addition, in some embodiments in generating the treatment response predictive model 70/70', the method described above can further incorporate other clinical data to form multimodal system. For example, known rating scale questionnaires, genetic information, blood test results, or other relevant information can be incorporated in generating the treatment response predictive model 70/70', which could further enhance accuracy of the model in predicting a treatment outcome with additional corroborating information.

Figure 10:
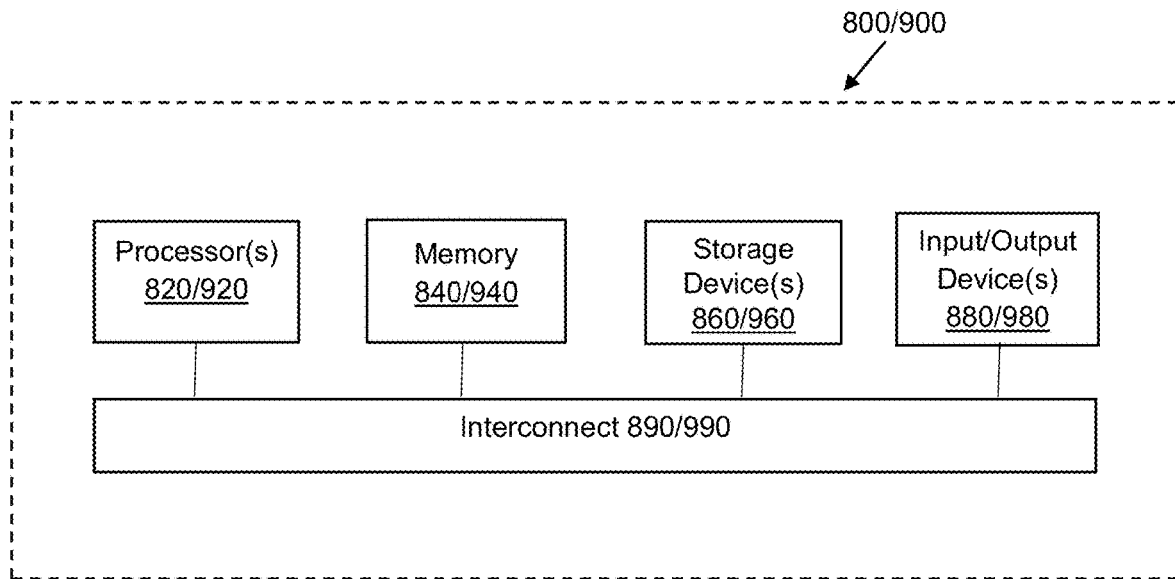
FIG. 10 is a block schematic diagram of computer system(s) configured according to the present disclosure.

In another aspect, the present invention further provides a system that carries out the methods described in the above embodiments. FIG. 10 shows a block diagram illustrating example computer systems 800 and 900 that can be used to implement the methods described above. As shown in FIG. 10, each of the computer systems 800 and 900 can include a processor 820/920, a memory 840/940, a storage device 860/960, and input/output devices 880/980. The respective processor, the memory, the storage device, and the input/output devices are interconnected by a bus or an interconnect network 890/990. The processor 820/920 enables processing instructions for execution in the respective computer system 800/900. Such executed instructions can implement the methods and the machine learning model described above. In some embodiments, the processor 820/920 may be a single-threaded processor, or alternately, a multi-threaded processor. The processor 820/920 is capable of processing instructions stored in the respective memory 840/940 and/or on the respective storage device 860/960 to display information for a user interface provided through the respective input/output device 880/980.

The memory 840/940 is a computer readable medium, such as volatile or non-volatile, that stores information in the respective computer system 800/900. The storage device 860/960 is capable of providing persistent storage for the respective computer system 800/900. The storage device 860/960 can be a solid state drive, a floppy disk device, a hard disk device, an optical disk device, or a tape device, or other suitable persistent storage means. The input/output device 880/980 provides input/output operations for the respective computer system 800/900. In some embodiments, the input/output device 880/980 includes a keyboard and/or pointing device. In various implementations, the input/output device 880/980 includes a display unit for displaying graphical user interfaces. In some embodiments, the input/output device 880/980 can provide input/output operations for a network device. For example, the input/output device 880/980 can include Ethernet ports or other networking ports to communicate with one or more wired and/or wireless networks (for example, a local area network (LAN), a wide area network (WAN), or the Internet).

In some embodiments, the computer system 800/900 can be used to execute various interactive computer software applications that can be used for organization, analysis and/or storage of data in various formats. Alternatively, the computer system 800/900 can be used to execute any type of software applications. These applications can be used to perform various functionalities, for example, planning functionalities (such as generating, managing, editing of spreadsheet documents, word processing documents, etc.), computing functionalities, communications functionalities, etc. The applications can include various add-in functionalities or can be standalone computing products and/or functionalities. Upon activation within the applications, the functionalities can be used to generate the user interface provided through the input/output device 880/900. The user interface can be generated and presented to a user by the computer system 800/900, for example, on a computer screen monitor.

Figure 11:
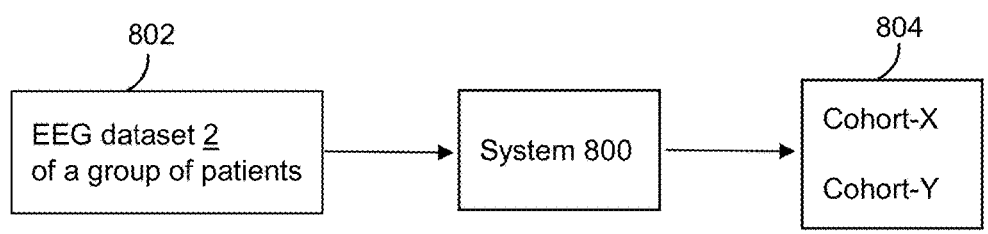
FIG. 11 is a schematic diagram illustrating a system in one embodiment of the present invention.

FIG. 11 schematically illustrates a function of system 800, which processes patient EEG dataset 2 from a group of psychiatric disorder patients as the input 802 and produces identified cohorts, Cohorts X and Y (box 804) of the group of patients.

More specifically, in some embodiments, the computer system 800 carries out operations illustrated in FIGS. 1 and 2, which includes: analyzing at least one type of brain region mutual interaction characteristics 20 using a scalp EEG data from each of a group of psychiatric disorder patients and obtaining a set of brain region mutual interaction feature matrices (MIFMs) 30 of each patient, performing a multi-frequency band generalized eigenvalue decomposition (GED) process 40 to the set of mutual interaction feature matrices 30 of each patient to extract prominent mutual interaction features and generating an eigenvector assembly matrix (EAM) 50 of each patient, and applying a machine learning algorithm to the eigenvector assembly matrices 50 from the group of patients to identify cohorts among these patients.

Moreover, in further embodiments, the computer system 800 carries out operations illustrated in FIG. 5, in which upon completion of process 300, a machine learning algorithm 60 can be applied to the hybrid eigenvector assembly matrix (EAMh) 50*h* from the group of patients to identify cohorts of the psychiatric disorder patients.

Figure 12:
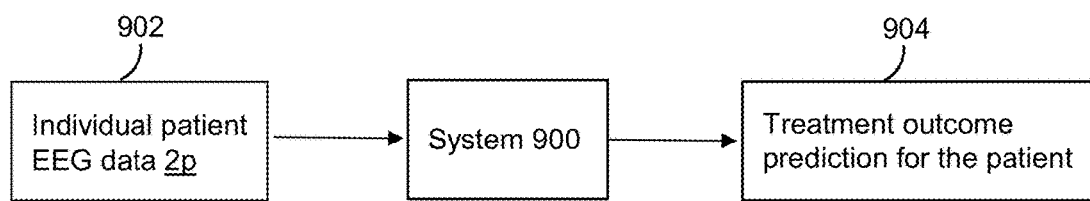
FIG. 12 is a schematic diagram illustrating a system in a further embodiment of the present invention.

FIG. 12 schematically illustrates a function of system 900, which processes an EEG data 2p from an individual patient as the input 902 and produces a treatment response prediction for the patient (box 904). Morse specifically, in some embodiments, the computer system 900 carries out operations as illustrated in process 400 in FIG. 6, which includes: analyzing at least one type brain region mutual interaction characteristics 20 using a scalp EEG data 2p from a patient and obtaining a set of brain region mutual interaction feature matrices (MIFMs) 30, performing a multi-frequency band generalized eigenvalue decomposition (GED) process 40 to the set of mutual interaction feature matrices 30 to extract prominent mutual interaction features and generating an eigenvector assembly matrix (EAM) 50 of the patient, and applying a treatment response predictive model 70 to the eigenvector assembly matrix 50 to determine a treatment outcome prediction 80 for the patient.

Moreover, in further embodiments, the computer system 900 carries out operations illustrated in process 700 in FIG. 9, in which a treatment response predictive model 70' is applied to the hybrid eigenvector assembly matrix (EAMh) 50*h* of the patient to produce a treatment response prediction 80 for the patient.

The present invention has several significant advantages. As described above, the method described herein can effectively identify cohorts of psychiatric disorder patients by analyzing brain region mutual interaction characteristics using scalp EEG data of the patients. With the method described herein, patients with certain underlying neurological disorder can be effectively separated from those without the neurological disorders or those with other type of disorders. Therefore, the method described herein can provide objective physiological evidence for psychiatric drug development, diagnosis and treatment, as well as for neuroscience, psychiatry, and psychology research.

Moreover, as described above and demonstrated by the example below, using the method described herein, the actual effect of a medicine under clinical trial can be clearly recognized with demonstrable statistical significance and effect size. As shown, the method described herein is capable of identifying cohorts with large effect size, as measured by Cohen's d value. In general, in clinical trials doubling of Cohen's d value will reduce the needed sample size by a factor of 4. By identifying suitable cohorts, the method described herein can effectively reduce necessary clinical trial size by as much as 75%, which will result in a significant cost saving, shortening of clinical trial time, and increase of trial success rate. Therefore, the method described herein can be used to improve quality and effectiveness of clinical trials for treating psychiatric disorder patients.

On the other hand, as described above, the present invention provides a method and system for determining a treatment outcome prediction for patients. This has a wide range of applications in the field of psychiatric diagnosis and treatment. The above described system can be provided to hospitals, clinics, doctor's offices, and other facilities to assist medical professionals for determining suitable clinical treatment to their patients.

The method described herein is advantageous over MRI in terms of the capability of discovering more of meaningful information, especially time-related information, by either waveform analysis and/or statistical analysis. Moreover, without relying on MRI data, the method described herein has a substantially lower cost and requires less operational time. In comparison to MRI, it is substantially more convenient to acquire EEG data. EEG test only requires a quiet room and briefcase-size equipment. In addition to hospitals and laboratories, EEG test can be conducted in doctor's offices, emergency room, Intensive Care Unit, and ambulance. Moreover, home or wearable EEG device are also available for continuous data collection. On the other hand, although the method described herein operates independently without relying on MPR, when MRI data is available, the method described herein can also incorporate MRI data in the process of analyzing one or more types of brain region mutual interaction characteristics.

Furthermore, the method described herein has a low requirement for computing resources. In addition, as described above, the method described herein can also be readily combined with other types of clinical data or tools to form multimodal systems to further enhance accuracy or effect size of the method described herein with additional corroborating information.

EXAMPLE

The method described above in reference to FIGS. 1, 2 and 5 was used in evaluation of results of a previous clinical trial for an anti-depression drug for identifying responsive and non-responsive cohorts of the participating patients.

All participating patients were clinically diagnosed as having major depressive disorder prior to selection for the clinical trial. The scalp EEG data of these patients were taken by four medical centers in different areas of the United States, and the four medical centers used different electroencephalography equipment. The scalp EEG data were collected prior to the patients' treatment phase of the clinical trial. The clinical trial had an eligible EEG dataset of 206 patients.

In the clinical trial, the participating patients were divided into two groups: a treatment group of 100 patients and a placebo group of 106 patients. The patients in the treatment group were administered the anti-depression drug according to the treatment protocol of the clinical trial, and the patients in the placebo group were given a placebo.

The results of the anti-depression drug of the clinical trial was evaluated by analyzing reduction of HAM-D scores during the anti-depression drug treatment for all participants together. Hamilton rating scale for depression (HRSD), which is also called Hamilton depression rating scale and often abbreviated as HAM-D. Hamilton rating scale for depression is one of the longest standing, most widely used measures of depression severity in clinical practice. It is a clinician-administered assessment using a multiple-item questionnaire to rate severity of depression by probing mood, feelings of guilt, suicide ideation, insomnia, agitation or retardation, anxiety, weight loss, and somatic symptoms. The original 1960 version of the questionnaire contained 17 items. Each item on the questionnaire is scored on a 3 or 5 point scale, depending on the item. The higher the HAM-D score, the more severe the depression. The American Psychiatric Association (APA) and National Institute for Health & Clinical Excellence (NIHCE) of the UK established the levels of depression in relation to the 17 item HRSD, wherein the level of depression as classified in APA 2000 (NIHCE 2019) are: Not depressed: 0-7, Mild (subthreshold): 8-13, Moderate (mild): 14-18, Severe (moderate): 19-22, Very severe (severe): >23. In this example, the clinical trial used 17 item questionnaire and the HAM-D scores in FIG. 13 is shown as HAMD-17 scores.

Figure 13:
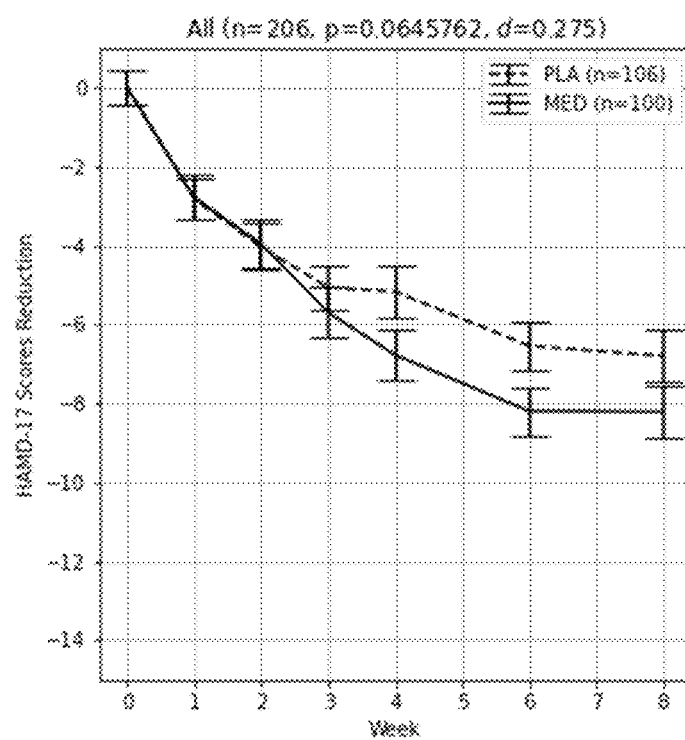
FIG. 13 shows results of a previous clinical trial of an anti-depression drug analyzed using Hamilton depression rating scale.

FIG. 13 shows the results of the clinical trial in a chart which depicts reduction of HAM-D scores over the time of treatment. In FIG. 13, the Y-axis is HAM-D score reduction and the X-axis is time in weeks. The solid line represents the result of the treatment group and the broken line represents the result of the placebo group. As shown in FIG. 13, collectively, the treatment group exhibited certain level of reduction in HAM-D score, however, the difference between the treatment and placebo group was not statistically significant ($p=0.0645762$). Therefore, the results of this clinical trial as shown in FIG. 13 failed to demonstrate the effect of the anti-depression drug in treating major depressive disorder.

The above descried method of the present invention was used to assess the results of the clinical trial using scalp EEG data from the participating patients. In this example, two types of brain region mutual interaction characteristics, power-envelope correlation and covariance, were analyzed using the EEG dataset of 206 patients in a process as illustrated in FIGS. 1, 2 and 5.

The EEG data of each patient was segmented into a plurality of epochs of 2 second length. First, a first set of brain region mutual interaction feature matrices (MIFM1s) was obtained from analysis of covariance for each epoch of the EEG data of a patient, with each matrix for one frequency band of the EEG data. The covariance was computed by the covariance function of open-source software Python package sklearn. Subsequently, a first multi-frequency band generalized eigenvalue decomposition (GED) process was carried out to the set of MIFM1s of each epoch, which generated a (35 frequency bands)×(56 channels) eigenvector assembly matrix (eam-e). Thereafter, the eigenvector assembly matrix (eam-e) of all epochs of the EEG of each patient was averaged to generate the eigenvector assembly matrix (EAM1) of the patient.

Next, a second set of brain region mutual interaction feature matrices (MIFM2s) was obtained from analysis of power-envelope correlation for each epoch of the EEG data of the same patient, with each matrix for one frequency band of the EEG data. The power-envelope correlation was computed using the function envelope_correlation in open-source Python package MNE.

Thereafter, the eigenvector assembly matrix (EAM1) of covariance and the mutual interaction feature matrices MIFM2s of power-envelope correlation from a selected frequency band are, respectively, flattened into two 1-dimensional matrices, which are then concatenated into one 1-dimensional matrix, namely a hybrid eigenvector assembly matrix (EAMh) of the patient. Subsequently, a clustering algorithm, K-means, was applied to the hybrid eigenvector assembly matrices (EAMh) of all participating patients to identify responsive and non-responsive cohorts of the participating patients.

FIGS. 14(A) and (B) show the results of identifying cohorts of major depressive disorder patients of the clinical trial using the present method. In FIGS. 14(A) and (B), X-axis and Y-axis, as well as their scale, are the same as in FIG. 13. Similarly, in both FIGS. 14(A) and (B), the solid line represents the result of the treatment group and the broken line represents the result of the placebo group. FIG. 14(A) shows the result of Cohort 1 as identified by the method described above, while FIG. 14(B) shows the result of Cohort 2.

As indicated in FIG. 14(A), 89 patients (n=89) were identified by the process described above as Cohort 1, and among them 39 patients were in the treatment group and 50 patients were in the placebo group. As shown in FIG. 14(A), in Cohort 1, the treatment group exhibited a significant reduction of HAM-D score over time in response to the anti-depression drug treatment, which was drastically different from the response of the placebo group. The difference between the treatment and placebo group was statistically significant ($p=0.0000011$), and effect size specified by Cohen's d value was large ($d=1.208$), indicating a large effect on the treatment group. It is noted that in interpreting Cohen's d value, commonly used interpretation is to refer to effect sizes as small ($d=0.2$), medium ($d=0.5$), and large ($d=0.8$) based on benchmarks suggested by Cohen.

On the other hand, 117 patients (n=117) in the clinical trial were identified as Cohort 2, see FIG. 14(B), and among them 61 patients were in the treatment group and 56 patients were in the placebo group. As shown in FIG. 14(B), in Cohort 2, the treatment group exhibited a similar pattern as the placebo group in their HAM-D score reduction over time in response to the anti-depression drug treatment. The difference between the treatment and placebo group was not statistically significant ($p=0.4679457$), and effect size was negative ($d=-0.144$), indicating that the treatment group had worse response than the placebo group.

As demonstrated in FIGS. 14(A) and (B), Cohort 1 patients and Cohort 2 patients had significantly different responses to the anti-depression drug treatment. The anti-depression drug treatment had a strong effect on Cohort 1 patients, while the same treatment had essentially no impact to the Cohort 2 patients. The treatment outcome of Cohort 1 patients showed evidently the anti-depression drug was effective for an identifiable population of major depressive disorder patients, and the anti-depression drug could be specifically purposed for this patient population.

Comparing the results in FIGS. 14(A) and (B) with that in FIG. 13, one can readily recognize the effectiveness of the present method in identifying responsive and non-responsive cohorts of a clinical treatment and its importance in assisting and guiding a meaningful clinical trial. The present method effectively extracts brain region mutual interaction features in scalp EEG data of major depressive disorder patients and uses these complex information embedded in patients' EEG data to differentiate a responsive population of major depressive disorder patients from others.

Moreover, in this example using the EEG dataset from the treatment group, a treatment response predictive model (TRPM) for predicting treatment outcome of the anti-depression drug in treating major depressive disorder was established. In this case, the treatment response predictive model 70/70' could be developed with the EEG dataset of the treatment group using the types of brain region mutual interaction characteristics analyzed, either independently (process 500 in FIG. 7) or in combination (process 600 in FIG. 8).

While the present invention has been described in detail and pictorially shown in the accompanying drawings, these should not be construed as limitations on the scope of the present invention, but rather as an exemplification of preferred embodiments thereof. It will be apparent, however, that various modifications and changes can be made within the spirit and the scope of this invention as described in the above specification and defined in the appended claims and their legal equivalents.

What is claimed is:

1. A method for determining a treatment outcome prediction for a patient using electroencephalograph, the method comprising:
    receiving a scalp electroencephalograph (EEG) data of a patient who is diagnosed with a psychiatric disorder, prior to the patient receiving a clinical treatment for the psychiatric disorder;
    analyzing at least one type of brain region mutual interaction characteristics using multiple frequency bands of the EEG data and generating a set of brain region mutual interaction feature matrices (MIFMs), each matrix for one of the multiple frequency bands;
    performing a multi-frequency band generalized eigenvalue decomposition (GED) process to the set of MIFMs to extract prominent mutual interaction features, thereby generating an eigenvector assembly matrix (EAM), wherein the multi-frequency band GED process comprises performing a generalized eigenvalue decomposition to each of the set of MIFMs to identify eigenvectors and corresponding eigenvalues for each of the MIFMs, extracting prominent eigenvectors of each of the multiple-frequency bands having corresponding eigenvalues that are larger than corresponding eigenvalues of other eigenvectors of each respective frequency band, and assembling the eigenvector assembly matrix (EAM) that contains the prominent eigenvectors of each of the multiple frequency bands;
    using a treatment response predictive model to analyze the eigenvector assembly matrix (EAM) and determining a treatment outcome prediction for the clinical treatment for the psychiatric disorder based on the EAM; and
    reporting the treatment outcome prediction for the patient, wherein when the treatment outcome prediction indicates the patient being a responsive subject, the clinical treatment for the psychiatric disorder is administered to the patient.

2. The method of claim 1, wherein the eigenvector assembly matrix (EAM) has a dimension of a (number of frequency bands)×(number of channels).

3. The method of claim 1, wherein the set of brain region mutual interaction feature matrices (MIFMs) is obtained for each epoch of the EEG data, and wherein the multi-frequency band GED process comprises performing a multi-frequency band generalized eigenvalue decomposition to the set of brain region mutual interaction feature matrices (MIFMs) of each epoch and assembling a (number of frequency bands)×(number of channels) eigenvector assembly matrix (eam-e), in which the eigenvector assembly matrix (eam-e) contains prominent mutual interaction features of each epoch, and averaging the eigenvector assembly matrix (eam-e) of all epochs, thereby generating the eigenvector assembly matrix (EAM) of the patient.

4. The method of claim 1, wherein in said generalized eigenvalue decomposition of each of the set of MIFMs, each MIFM, corresponding to one of the multiple frequency bands, is used against a broadband brain region mutual interaction feature matrix generated from broadband signals of the EEG data to extract the prominent eigenvectors from each MIFM.

5. The method of claim 1, wherein the method further comprises
    analyzing at least one further type of brain region mutual interaction characteristics using the multiple frequency bands of the EEG data of the patient and obtaining at least one further set of brain region mutual interaction feature matrices (MIFM2s), each matrix thereof for one of the multiple frequency bands; and
    combining the EAM with the MIFM2s to form a hybrid eigenvector assembly matrix (EAMh), and wherein the treatment response predictive model is used to analyze the EAMh to determine the treatment outcome prediction for the patient.

6. The method of claim 1, wherein the method further comprises
    analyzing at least one further type of brain region mutual interaction characteristics using the multiple frequency bands of the EEG data of the patient and obtaining at least one further set of brain region mutual interaction feature matrices (MIFM2s), each matrix thereof for one of the multiple frequency bands;
    performing a further multi-frequency band GED process to the at least one further set of MIFM2s and generating at least one further eigenvector assembly matrix (EAM2); and
    combining the EAM with the EAM2 to form a hybrid eigenvector assembly matrix (EAMh), and wherein the treatment response predictive model is used to analyze the EAMh to determine the treatment outcome prediction for the patient.

7. The method of claim 1, wherein the patient is a COVID-19 patient and has a psychiatric disorder symptom originated from COVID-19.

8. A method of generating a treatment response predictive model using electroencephalograph, comprising:
    analyzing at least one type of brain region mutual interaction characteristics using multiple frequency bands of a scalp electroencephalograph (EEG) data that is collected from each of a plurality of patients, who are diagnosed with a psychiatric disorder, prior to receiving a clinical treatment for the psychiatric disorder, and generating a set of brain region mutual interaction feature matrices (MIFMs) of each patient, each matrix for one of the multiple frequency bands;

performing a multi-frequency band generalized eigenvalue decomposition (GED) process to the set of brain region mutual interaction feature matrices (MIFMs) of each patient to extract prominent mutual interaction features, thereby generating an eigenvector assembly matrix (EAM) of each patient, wherein the multi-frequency band GED process comprises performing a generalized eigenvalue decomposition to each of the set of MIFMs to identify eigenvectors and corresponding eigenvalues for each of the MIFMs, extracting prominent eigenvectors of each of the multiple-frequency bands having corresponding eigenvalues that are larger than corresponding eigenvalues of other eigenvectors of each respective frequency band, and assembling the eigenvector assembly matrix (EAM) that contains the prominent eigenvectors of each of the multiple frequency bands; and using a machine learning algorithm, with the eigenvector assembly matrices (EAMs) obtained from the plurality of patients and responses of the plurality of patients to the clinical treatment for the psychiatric disorder as inputs, to differentiate the EAMs of the plurality of patients, thereby generating a treatment response predictive model capable of determining a treatment outcome prediction of the clinical treatment for the psychiatric disorder based on the EAM of a subject of interest, wherein when the treatment outcome prediction indicates the subject of interest being a responsive subject, the clinical treatment for the psychiatric disorder is administered to the subject of interest.

9. The method of claim 8, wherein the eigenvector assembly matrix (EAM) of each patient has a dimension of a (number of frequency bands)×(number of channels).

10. The method of claim 8, wherein the set of brain region mutual interaction feature matrices (MIFMs) is obtained for each epoch of the EEG data, and wherein the multi-frequency band GED process comprises performing a multi-frequency band generalized eigenvalue decomposition to the set of brain region mutual interaction feature matrices (MIFMs) of each epoch and assembling a (number of frequency bands)×(number of channels) eigenvector assembly matrix (eam-e), in which the eigenvector assembly matrix (eam-e) contains prominent mutual interaction features of each epoch, and averaging the eigenvector assembly matrix (eam-e) of all epochs, thereby generating the eigenvector assembly matrix (EAM) of each patient.

11. The method of claim 8, wherein in said generalized eigenvalue decomposition of each of the set of MIFMs, each MIFM, corresponding to one of the multiple frequency bands, is used against a broadband brain region mutual interaction feature matrix generated from broadband signals of the EEG data to extract the prominent eigenvectors from each MIFM.

12. The method of claim 8, wherein the method further comprises
analyzing at least one further type of brain region mutual interaction characteristics using the multiple frequency bands of the EEG data of each patient and obtaining at least one further set of brain region mutual interaction feature matrices (MIFM2s), each matrix thereof for one of the multiple frequency bands; and
combining the EAM with the MIFM2s to form a hybrid eigenvector assembly matrix (EAMh) of each patient, and wherein the hybrid eigenvector assembly matrices (EAMhs) obtained from the plurality of patients are used by the machine learning algorithm to generate the treatment response predictive model of the clinical treatment.

13. The method of claim 8, wherein the method further comprises
analyzing at least one further type of brain region mutual interaction characteristics using the multiple frequency bands of the EEG data of each patient and obtaining at least one further set of brain region mutual interaction feature matrices (MIFM2s), each matrix thereof for one of the multiple frequency bands;
performing a further multi-frequency band GED process to the at least one further set of MIFM2s and generating at least one further eigenvector assembly matrix (EAM2) of each patient; and
combining the EAM with the EAM2 to form a hybrid eigenvector assembly matrix (EAMh) of each patient, and wherein the hybrid eigenvector assembly matrices (EAMhs) obtained from the plurality of patients are used by the machine learning algorithm to generate the treatment response predictive model of the clinical treatment.

14. A system for determining a treatment outcome prediction for a patient using electroencephalograph, the system comprising: at least one data processor; and at least one memory storing instructions which, when executed by the at least one data processor, result in operations comprising:
analyzing at least one type of brain region mutual interaction characteristics using multiple frequency bands of a scalp electroencephalograph (EEG) data of a patient who is diagnosed with a psychiatric disorder, prior to the patient receiving a clinical treatment for the psychiatric disorder, and generating a set of brain region mutual interaction feature matrices (MIFMs), each matrix for one of the multiple frequency bands;
performing a multi-frequency band generalized eigenvalue decomposition (GED) process to the set of MIFMs to extract prominent mutual interaction features, thereby generating an eigenvector assembly matrix (EAM), wherein the multi-frequency band GED process comprises performing a generalized eigenvalue decomposition to each of the set of MIFMs to identify eigenvectors and corresponding eigenvalues for each of the MIFMs, extracting prominent eigenvectors of each of the multiple-frequency bands having corresponding eigenvalues that are larger than corresponding eigenvalues of other eigenvectors of each respective frequency band, and assembling the eigenvector assembly matrix (EAM) that contains the prominent eigenvectors of each of the multiple frequency bands;
using a treatment response predictive model to analyze the eigenvector assembly matrix (EAM) and determining a treatment outcome prediction for the clinical treatment for the psychiatric disorder based on the EAM; and
reporting the treatment outcome prediction for the patient, wherein when the treatment outcome prediction indicates the patient being a responsive subject, the clinical treatment for the psychiatric disorder is administered to the patient.

15. The system of claim 14, wherein the eigenvector assembly matrix (EAM) has a dimension of a (number of frequency bands)×(number of channels).

16. The system of claim 14, wherein the set of brain region mutual interaction feature matrices (MIFMs) is obtained for each epoch of the EEG data, and wherein the multi-frequency band GED process is performed by applying a multi-frequency band generalized eigenvalue decomposition to the set of brain region mutual interaction feature matrices (MIFMs) of each epoch and assembling a (number of frequency bands)×(number of channels) eigenvector assembly matrix (eam-e), in which the eigenvector assembly matrix (eam-e) contains prominent mutual interaction features of each epoch, and averaging the eigenvector assembly matrix (eam-e) of all epochs, thereby generating the eigenvector assembly matrix (EAM) of the patient.

17. The system of claim 14, wherein in said generalized eigenvalue decomposition of each of the set of MIFMs, each MIFM, corresponding to one of the multiple frequency bands, is used against a broadband brain region mutual interaction feature matrix generated from broadband signals of the EEG data to extract the prominent eigenvectors from each MIFM.

18. The system of claim 14, wherein the system, when executed by the at least one data processor, further results in operations comprising:
  analyzing at least one further type of brain region mutual interaction characteristics using the multiple frequency bands of the EEG data of the patient and obtaining at least one further set of brain region mutual interaction feature matrices (MIFM2s), each matrix thereof for one of the multiple frequency bands; and
  combining the EAM with the MIFM2s to form a hybrid eigenvector assembly matrix (EAMh), and wherein the treatment response predictive model is used to analyze the EAMh to determine the treatment outcome prediction for the patient.

19. The system of claim 14, wherein the system, when executed by the at least one data processor, further results in operations comprising:
  analyzing at least one further type of brain region mutual interaction characteristics using the multiple frequency bands of the EEG data of the patient and obtaining at least one further set of brain region mutual interaction feature matrices (MIFM2s), each matrix thereof for one of the multiple frequency bands;
  performing a further multi-frequency band GED process to the at least one further set of MIFM2s and generating at least one further eigenvector assembly matrix (EAM2); and
  combining the EAM with the EAM2 to form a hybrid eigenvector assembly matrix (EAMh), and wherein the treatment response predictive model is used to analyze the EAMh to determine the treatment outcome prediction for the patient.

\* \* \* \* \*